(12) United States Patent
Paradis

(10) Patent No.: US 12,285,621 B2
(45) Date of Patent: *Apr. 29, 2025

(54) AUTOMATED RESUSCITATION SYSTEM INTEGRATING HEMODYNAMIC AND DEFIBRILLATORY CAPABILITIES

(71) Applicant: Norman Alan Paradis, Putney, VT (US)

(72) Inventor: Norman Alan Paradis, Putney, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/676,612

(22) Filed: Feb. 21, 2022

(65) Prior Publication Data

US 2022/0233875 A1   Jul. 28, 2022

Related U.S. Application Data

(63) Continuation of application No. 16/514,968, filed on Jul. 17, 2019, now Pat. No. 11,253,713.

(Continued)

(51) Int. Cl.
*A61N 1/00* (2006.01)
*A61B 5/318* (2021.01)
(Continued)

(52) U.S. Cl.
CPC .......... *A61N 1/39044* (2017.08); *A61B 5/318* (2021.01); *A61H 31/005* (2013.01)

(58) Field of Classification Search
CPC .... A61N 1/39044; A61N 1/3625–3629; A61N 1/046; A61N 1/0484; A61N 1/3925;
(Continued)

(56) References Cited

U.S. PATENT DOCUMENTS 2,699,163 A   1/1955   Engstrom
2,899,955 A   8/1959   Huxley, III et al.
(Continued)

FOREIGN PATENT DOCUMENTS

EP   2709581 B1   7/2017
KR   101383051 B   4/2014
(Continued)

OTHER PUBLICATIONS

Plaisance, M.D., Patrick, A Comparison of Standard Cardiopulmonary Resuscitation and Active Compression- Decompression Resuscitation for Out-of-Hospital Cardiac Arrest, New England Journal of Medicine, vol. 341, No. 8, Aug. 19, 1999, pp. 569-575.
(Continued)

*Primary Examiner* — Scott M. Getzow

(74) *Attorney, Agent, or Firm* — Nathaniel A. Wickliffe, Patent Attorney

(57) ABSTRACT

An automated resuscitation system is provided, which can improve the outcome of patients suffering ventricular fibrillation or the ventricular tachycardia variants of cardiac arrest. This outcome can be achieved by a device that integrates automatic mechanical or pneumatic capability with electrical countershock capability such that the probability of defibrillation or cardioversion with return of spontaneous circulation is increased.

20 Claims, 11 Drawing Sheets

Related U.S. Application Data

(60) Provisional application No. 62/699,647, filed on Jul. 17, 2018.

(51) Int. Cl.
*A61H 31/00* (2006.01)
*A61N 1/39* (2006.01)

(58) Field of Classification Search
CPC ............. A61N 1/3987; A61H 31/005; A61H 2031/003; A61H 9/0078; A61H 2201/0103; A61H 2201/013; A61H 2201/1238; A61H 2201/1246; A61H 2201/1621; A61H 2201/1638; A61H 2201/5007; A61H 2201/5023; A61H 2201/5046; A61H 2203/0456; A61H 2205/06; A61H 2205/083; A61H 2205/084; A61H 2205/106; A61H 2230/206; A61H 31/006; A61H 2201/1642; A61H 2230/105; A61B 5/318; A61B 5/0205

See application file for complete search history.

(56) References Cited

U.S. PATENT DOCUMENTS

| | | | |
|---|---|---|---|
| 3,364,924 A | 1/1968 | Barkalow | |
| 3,481,327 A | 12/1969 | Drennen | |
| 3,683,655 A | 8/1972 | White et al. | |
| 4,198,963 A | 4/1980 | Barkalow et al. | |
| 4,349,015 A | 9/1982 | Alferness | |
| 4,397,306 A | 8/1983 | Weisfeldt et al. | |
| 4,424,806 A | 1/1984 | Newman et al. | |
| 4,664,098 A | 5/1987 | Woudenberg et al. | |
| 4,770,164 A | 9/1988 | Lach et al. | |
| 4,838,263 A | 6/1989 | Warwick et al. | |
| 4,840,167 A | 6/1989 | Olsson et al. | |
| 4,928,674 A * | 5/1990 | Halperin | A61H 31/008 600/510 |
| 5,076,259 A | 12/1991 | Hayek | |
| 5,078,134 A * | 1/1992 | Heilman | A61N 1/046 607/142 |
| 5,222,478 A | 6/1993 | Scarberry et al. | |
| 5,454,779 A | 10/1995 | Lurie et al. | |
| 5,490,820 A | 2/1996 | Schock et al. | |
| 5,496,257 A | 3/1996 | Kelly | |
| 5,743,864 A | 4/1998 | Baldwin, II | |
| 5,769,800 A | 6/1998 | Gelfand et al. | |
| 6,171,267 B1 | 1/2001 | Baldwin, II | |
| 6,174,295 B1 | 1/2001 | Cantrell et al. | |
| 6,213,960 B1 | 4/2001 | Sherman et al. | |
| 6,224,562 B1 | 5/2001 | Lurie et al. | |
| 6,374,827 B1 * | 4/2002 | Bowden | A61H 9/0078 128/207.14 |
| 6,390,996 B1 | 5/2002 | Halperin et al. | |
| 6,393,316 B1 | 5/2002 | Gillberg et al. | |
| 6,418,342 B1 | 7/2002 | Owen et al. | |
| 6,427,685 B1 | 8/2002 | Ray | |
| 6,752,771 B2 | 6/2004 | Rothman et al. | |
| 6,827,695 B2 | 12/2004 | Palazzolo et al. | |
| 6,869,409 B2 | 3/2005 | Rothman et al. | |
| 7,032,596 B2 | 4/2006 | Thompson et al. | |
| 7,220,235 B2 | 5/2007 | Geheb et al. | |
| 8,433,412 B1 * | 4/2013 | Westlund | A61N 1/36542 607/42 |
| 8,478,401 B2 | 7/2013 | Freeman | |
| 8,795,208 B2 | 8/2014 | Walker | |
| 9,474,892 B2 | 10/2016 | Chang et al. | |
| 10,245,209 B2 | 4/2019 | Lurie et al. | |
| 10,772,793 B2 | 9/2020 | Paradis | |
| 10,888,493 B2 | 1/2021 | Freeman et al. | |
| 2001/0007928 A1 | 7/2001 | Hansen | |
| 2002/0026131 A1 | 2/2002 | Halperin | |
| 2003/0004445 A1 | 1/2003 | Hall et al. | |
| 2004/0162510 A1 * | 8/2004 | Jayne | A61H 31/005 601/44 |
| 2004/0230140 A1 | 11/2004 | Steen | |
| 2006/0089574 A1 | 4/2006 | Paradis | |
| 2007/0010765 A1 | 1/2007 | Rothman et al. | |
| 2007/0032829 A1 | 2/2007 | Ostroff | |
| 2007/0060785 A1 | 3/2007 | Freeman et al. | |
| 2007/0225623 A1 | 9/2007 | Freeman | |
| 2007/0299473 A1 * | 12/2007 | Matos | A61N 1/3904 607/9 |
| 2008/0097534 A1 | 4/2008 | Myklebust et al. | |
| 2008/0275371 A1 | 11/2008 | Hoffmann | |
| 2010/0004572 A1 | 1/2010 | King | |
| 2012/0016179 A1 | 1/2012 | Paradis et al. | |
| 2012/0116272 A1 | 5/2012 | Hampton et al. | |
| 2012/0146797 A1 * | 6/2012 | Oskin | A61B 5/318 340/573.1 |
| 2014/0094724 A1 | 4/2014 | Freeman | |
| 2014/0155792 A1 | 6/2014 | Karve et al. | |
| 2014/0213942 A1 | 7/2014 | Hanson | |
| 2014/0336546 A1 | 11/2014 | Chapman et al. | |
| 2014/0358047 A1 | 12/2014 | Lurie | |
| 2015/0094624 A1 | 4/2015 | Illindala | |
| 2015/0265497 A1 | 9/2015 | Kaufman et al. | |
| 2016/0317385 A1 | 11/2016 | Salcido et al. | |
| 2016/0361228 A1 | 12/2016 | Paradis et al. | |
| 2017/0035650 A1 | 2/2017 | Taylor et al. | |
| 2017/0266078 A1 | 9/2017 | Jayne et al. | |
| 2018/0168922 A1 | 6/2018 | Chapman et al. | |
| 2019/0091099 A1 | 3/2019 | Nilsson et al. | |
| 2019/0117501 A1 | 4/2019 | Chapman et al. | |

FOREIGN PATENT DOCUMENTS

| | | |
|---|---|---|
| KR | 20160146462 A | 12/2016 |
| WO | 9628128 A1 | 9/1996 |
| WO | 9965560 A2 | 12/1999 |
| WO | 2010099628 A1 | 9/2010 |
| WO | 2014051934 A1 | 4/2014 |
| WO | 2015048347 A1 | 4/2015 |

OTHER PUBLICATIONS

Plaisance, P., et al. "Use of an inspiratory impedance threshold device on a facemask and endotracheal tube to reduce intrathoracic pressures during the decompression phase of active compression-decompression cardiopulmonary resuscitation." Crit Care Med. 33.5 (2005): 990-94.

Qvigstad et al., "Clinical pilot study of different hand positions during manual chest compressions monitored with capnography", Resuscitation 84 (2013) 1203-1207, www.elsevier.com/locate/resuscitation.

Ralston, Sandra H., Cardiopulmonary Resuscitation with Interposed Abdominal Compression in Dogs, Anesthesia and Analgesia, vol. 61, No. 8, Aug. 1982, pp. 645-651.

Ramirez et al., "Effect of Applying Force to Self-Adhesive Electrodes on Transthoracic Impedance: Implications for Electrical Cardioversion", Pace, vol. 39, Oct. 2016, pp. 1141-1147.

Rubertsson S, Lindgren E, Smekal D et al. "Mechanical chest compressions and simultaneous defibrillation vs conventional cardiopulmonary resuscitation in out-of-hospital cardiac arrest: the LINC randomized trial". JAMA 2014; 311(1):53-61.

Rudikoff, M. T., et al. "Mechanisms of Blood Flow During Cardiopulmonary Resuscitation." Circulation 61 (1980): 345-52.

Sanders AB, Kern KB, Ewy GA, Atlas M, Bailey L. "Improved resuscitation from cardiac arrest with open-chest massage". Ann Emerg Med 1984; 13(9 Pt 1):672-675.

Sanders, A.B., K.B. Kern, C.W. Otto, M.M. Milander, and G.A. Ewy. 1989. 'End-tidal carbon dioxide monitoring during cardiopulmonary resuscitation. A prognostic indicator for survival.', JAMA, 262: 1347-51.

Segal, M.D., PhD, Nicolas, Intermittent Positive-Pressure Ventilation, Chest Compression Synchronized Ventilation, Bilevel Ventilation, Continuous Chest Compression, Active Compression Decom-

(56) References Cited

OTHER PUBLICATIONS pression, and Impedance Threshold Device—The Complexity of Ventilation During Cardiopulmonary Resuscitation, Critical Care Medicine, Feb. 2014, vol. 42, No. 2, pp. 480-481.

Shinar Z, Bellezzo J, Paradis N et al. "Emergency department initiation of cardiopulmonary bypass: a case report and review of the literature". J Emerg Med 2012; 43(1):83-86.

Stephenson HE, Corsan Reed L, Hinton JW. "Some Common Denominators in 1200 cases of cardiac arrest". Ann Surg 1953; 137:731-744.

Stiell IG, Nichol G, Leroux BG et al. "Early versus later rhythm analysis in patients with out-of-hospital cardiac arrest". N Engl J Med 2011; 365(9):787-797.

Vector Definition; 2020; Merriam-Webster; https://www.merriam-webster.com/dictionary/vector (Year: 2020).

Voorhees, PhD, William D. et al, Improved Oxygen Delivery During Cardiopulmonary Resuscitation with Interposed Abdominal Compressions, Annals of Emergency Medicine, 12:Mar. 3, 1983, pp. 128-135.

Wang, M.D., Chih-Hung, et al, Active Compression-Decompression Resuscitation and Impedance Threshold Device for Out-of-Hospital Cardiac Arrest: A Systematic Review and Metaanalysis of Randomized Controlled Trials, Critical Sare Medicine, Apr. 2015, vol. 43, No. 4, pp. 889-896.

Weisfeldt, M.D., M.L., et al, Increased intrathoracic pressure—no direct heart compression-causes the rise in intrathoracic vascular pressures during CPR in dogs and pigs, Critical Care Medicine, pp. 377-378, May 1981.

Wik L, Olsen JA, Persse D et al. "Manual vs. integrated automatic load-distributing band CPR with equal survival after out of hospital cardiac arrest. The randomized CIRC trial". Resuscitation 2014; 85(6):741-748.

Wolcke, Md., Benno G., et al, Comparison of Standard Cardiopulmonary Resuscitation Versus the Combination of Active Compression-Decompression Cardiopulmonary Resuscitation and an Inspiratory Impedance Threshold Device for Out-of-Hospital Cardiac Arrest, Circulation, 2003, pp. 108, 2201-2205.

Xie, Z., Q. Yang, M. Li, Z. Huang, Y. Wang, Q. Ling, W. Tang, and Z. Yang. 2018. 'Amplitude screening improves performance of AMSA method for predicting success of defibrillation in swine model', Am J Emerg Med.

Yang, Z., et al. A tourniquet assisted cardiopulmonary resuscitation augments myocardial perfusion in a porcine model of cardiac arrest, Resuscitation 86 (2015) 49-53.

Yeung, J., et al, The use of CPR feedback/prompt devices during training and CPR performance: A systematic review, Resuscitation, 80, pp. 743-751, 2009.

Zoll, P. M., A. J. Linenthal, W. Gibson, M. H. Paul, and L. R. Norman. 1956. 'Termination of ventricular fibrillation in man by externally applied electric countershock', N Engl J Med, 254: 727-32.

Abella, Benjamin S. et al, CPR quality improvement during in-hospital cardiac arrest using a real-time audiovisual feedback system, Resuscitation, 2007, 73, pp. 54-61.

Aiello et al., "Real-time ventricular fibrillation amplitude-spectral area analysis to guide timing of shock delivery improves defibrillation efficacy during cardiopulmonary resuscitation in swine", Journal of the American Heart Association, DOI: 10.1161/JAHA. 117.006749, pp. 1-15, (2021).

Arntz, H.R., et al. Phased Chest and Abdominal Compression-Decompression Versus Conventional Cardiopulmonary Resuscitation in Out-of-Hospital Cardiac Arrest, American Heart Association, Inc., Aug. 14, 2001, pp. 768-772.

Aufderheide, T. P., et al. "Clinical evaluation of an inspiratory impedance threshold device during standard cardiopulmonary resuscitation in patients with out-of-hospital cardiac arrest." Crit Care Med. 33.4 (2005): 734-40.

Babbs, MD, Charles F., Preclinical Studies of Abdominal Counterpulsation in CPR, Annals of Emergency Medicine, 13: Sep. 9, 1984, pp. 761-763.

Barkalow, B. H. "Comparison of miniaturized pneumatic chest compressor to Thumper." Resuscitation 79.3 (2008): 509.

Beck, C. S., E. C. Weckesser, and F. M. Barry. 1956. 'Fatal heart attack and successful defibrillation; new concepts in coronary artery disease', J Am Med Assoc, 161: 434-6.

Berkowitz, Ivor D., et al, Blood Flow during Cardiopulmonary Resuscitation with Simultaneous Compression and Ventilation in Infant Pigs, Pediatric Research, 1989, vol. 26, No. 6, pp. 558-564.

Bircher, N., et al, Do Intrathoracic Pressure Fluctuation or Heart Compressions Move Blood During External Cardiopulmonary Resuscitation (CPR)?, Resuscitation Research Center and the Department of Anesthesiology, University of Pittsburgh, ASA Abstract, V53, No. 3, Sep. 1980.

Cabanas, J. G., J. B. Myers, J. G. Williams, V. J. De Maio, and M. W. Bachman. 2015. 'Double Sequential External Defibrillation in Out-of-Hospital Refractory Ventricular Fibrillation: A Report of Ten Cases', Prehosp Emerg Care, 19: 126-30.

Callaway, Clifton W.; Why We Should No. Longer Terminate Resuscitations after 20 Minutes; Mar. 2, 2016; Journal of Emergency Medical Services; vol. 41, Issue 3; (Year: 2016).

Cave DM, Gazmuri RJ, Otto CW et al. "Part 7: CPR techniques and devices: 2010 American Heart Association Guidelines for Cardiopulmonary Resuscitation and Emergency Cardiovascular Care". Circ 2010; 122(18 Suppl 3): S720-S728.

Chan PS, McNally B, Tang F, Kellermann A. "Recent trends in survival from out-of-hospital cardiac arrest in the United States" Circ 2014; 130(21):1876-1882.

Cohen, Todd J., et al, Active Compression-Decompression Resuscitation: A Novel Method of Cardiopulmonary Resuscitation, American Heart Journal, Nov. 1992, pp. 1145-1150.

Cohen, Todd J., et al., Active Compression-Decompression, a New Method of Cardiopulmonary Resuscitation, JAMA, Jun. 3, 1992, vol. 267, No. 21, pp. 2916-2923.

Deakin, C. D., R. M. McLaren, G. W. Petley, F. Clewlow, and M. J. Dalrymple-Hay. 1998. 'Effects of positive end-expiratory pressure on transthoracic impedance—implications for defibrillation', Resuscitation, 37: 9-12.

Esibov A, Banville I, Chapman FW, Boomars R, Box M, Rubertsson S. "Mechanical chest compressions improved aspects of CPR in the LINC trial". Resuscitation 2015; 91:116-121.

Ewy, G.A., D.A. Hellman, S. McClung, and D. Taren. 1980. 'Influence of ventilation phase on transthoracic impedance and defibrillation effectiveness', Crit. Care Med, 8: 164-66.

Haas, Thorsten, et al, Revisiting the cardiac versus thoracic pump mechanism during cardiopulmonary resuscitation, Resuscitation, 58, Nov. 5, 2002, pp. 113-116.

Hallstrom A, Rea TD, Sayre MR et al. "Manual chest compression vs use of an automated chest compression device during resuscitation following out-of-hospital cardiac arrest: a randomized trial". JAMA 2006; 295(22):2620-2628.

Halperin, H. R., et al. "Cardiopulmonary resuscitation with a novel chest compression device in a porcine model of cardiac arrest: improved hemodynamics and mechanisms." J.Am.Coll.Cardiol. 44.11 (2004): 2214-20.

Halperin, M.D., Henry R., A Preliminary Study of Cardiopulmonary Resuscitation by Circumferential Compression of the Chest with use of a Pneumatic Vest, The New England Journal of Medicine, vol. 329 No. 11, Sep. 9, 1993, pp. 762-768.

Hostler D, Everson-Stewart S, Rea TD et al. "Effect of real-time feedback during cardiopulmonary resuscitation outside hospital: prospective, cluster-randomised trial". BMJ 2011; 342:d512.

Jenkins, Constance, et al, Effects of the ResQPOD on Kinetics, Hemodynamics of Vasopressin, and Survivability in a Porcine Cardiac Arrest Model, Military Medicine, vol. 180, Sep. 2015, pp. 1011-1016.

Kerber, R. E., J. D. Bourland, M. J. Kallok, P. Hite, B. Pritchard, F. Charbonnier, C. Birkett, K. Fox-Eastham, and R. A. Kieso. 1990. 'Transthoracic defibrillation using sequential and simultaneous dual shock pathways: experimental studies', Pacing Clin Electrophysiol, 13: 207-17.

Kerber, R. E., J. Grayzel, R. Hoyt, M. Marcus, and J. Kennedy. 1981. 'Transthoracic resistance in human defibrillation. Influence of

(56) References Cited

OTHER PUBLICATIONS body weight, chest size, serial shocks, paddle size and paddle contact pressure', Circulation, 63: 676-82.

Kerber, R.E., K.T. Spencer, M.J. Kallok, C. Birkett, R. Smith, D. Yoerger, and R.A. Kieso. 1994. 'Overlapping sequential pulses. A new waveform for transthoracic defibrillation', Circ, 89: 2369-79.

Kirchhof, P., L. Eckardt, P. Loh, K. Weber, R. J. Fischer, K. H. Seidl, D. Bocker, G. Breithardt, W. Haverkamp, and M. Borggrefe. 2002. 'Anterior-posterior versus anterior-lateral electrode positions for external cardioversion of atrial fibrillation: a randomised trial', Lancet, 360: 1275-9.

Kleinman, Monica E., et al, Part 5: Adult Basic Life Support and Cardiopulmonary Resuscitation Quality: 2015 American Heart Association Guidelines Update for Cardiopulmonary Resuscitation, and Emergency Cardiovascular Care, Circulation, 2015, 132, S414-S435.

Kouwenhoven, Jude; Knickerbocker, Cardiac Arrest—The Science and Practice of Resuscitation Medicine, (19600000), p. 96, (2020).

Kouwenhoven, W.B Closed-Chest Cardiac Massage, JAMA, Jul. 9, 1960, vol. 173, No. 10, pp. 1064-1067.

Lafuente-Lafuente et al., "Active chest compression-decompression for cardiopulmonary resuscitation (Review)," The Cochrane Collaboration, 2009, Issue 3 (40 pages).

Li, Y., H. Wang, J. H. Cho, W. Quan, G. Freeman, J. Bisera, M. H. Weil, and W. Tang. 2010. 'Defibrillation delivered during the upstroke phase of manual chest compression improves shock success', Crit Care Med, 38: 910-5.

Liao et al., "Manual versus mechanical cardiopulmonary resuscitation. An experimental study in pigs", BMC Cardiovascular Disorders, Oct. 2010, 10:53, http://www.biomedcentral.com/1471-2261/10/53 (8 pages).

Lurie et a., "Improving active compression-decompression resuscitation with an inspiratory impedance valve", originally published Mar. 15, 1995, https://doi.org/10.1161/01.CIR.91.6.1629, Circulation. 1995; 91:1629-1632.

Lurie et al., "Improving standard cardiopulmonary resuscitation with an inspiratory impedance threshold valve in a porcine model of cardiac arrest", Anesth Analg 2001; 93:649-655.

Lurie, K.G., Improving active compression-decompression cardiopulmonary resuscitation with an inspiratory impedance value, Abstract Circulation 1995; 91/6 (1 page abstract).

McClung, Christian D., et al.; Interposed Abdominal Compression CPR for an Out-of-Hospital Cardiac Arrest Victim Failing Traditional CPR; Oct. 20, 2015; Western Journal of Emergency Medicine; vol. XVI, No. 5; 690-692 (Year: 2015).

McDonald, M.D., John L, Systolic and Mean Arterial Pressures During Manual and Mechanical CPR in Humans, Annals of Emergency Medicine, 11:Jun. 6, 1982, pp. 292-295.

Michael, John R., et al, Mechanisms by with epinephrine augments cerebral and myocardial perfusion during cardiopulmonary resuscitation in dogs, Circulation 69, No. 4, 822-834, 1984.

Neumann T, Gruenewald M, Lauenstein C, Drews T, Iden T, Meybohm P. "Hands-on defibrillation has the potential to improve the quality of cardiopulmonary resuscitation and is safe for rescuers—a preclinical study". J Am Heart Assoc 2012; 1(5):e001313.

Niemann Md., James T., Cough-CPR, Documentation of systemic perfusion in man and in an experimental model: a window to the mechanism of blood flow in external CPR, Critical Care Medicine, vol. 8, No. 3, pp. 141-146, Mar. 1980.

Ong ME, Annathurai A, Shahidah A et al. "Cardiopulmonary resuscitation interruptions with use of a load-distributing band device during emergency department cardiac arrest". Ann Emerg Med 2010; 56(3):233-241.

Ong, M. E., et al. "Use of an automated, load-distributing band chest compression device for out-of-hospital cardiac arrest resuscitation." JAMA 295.22 (2006): 2629-37.

Paradis M.D., Norman A., Simultaneous Aortic, Jugular Bulb, and Right Atrial Pressures During Cardiopulmonary Resuscitation in Humans, Insights Into Mechanisms, Circulation, vol. 80, No. 2, Aug. 1989.

Paradis, N. A. "Is this the next step for CPR?" Am. J. Emerg. Med. 18 34.1 (2016): 97-99.

Paradis, N. A., et al. "Coronary perfusion pressure during external chest compression in pseudo-EMD, comparison of systolic versus diastolic synchronization." Resuscitation 83.10 (2012): 1287-91.

Paradis, Norman A, et al, Cardiac Arrest, the Science and Practice of Resuscitation Medicine, 2nd edition, Cambridge University Press 2007.

Plaisance et al., "Evaluation of an impedance threshold device in patients receiving active compression-decompression cardiopulmonary resuscitation for out of hospital cardiac arrest", Elsevier, Resuscitation 61 (2004) 265-271, www.elsevier.com/locate/resuscitation.

Plaisance P, Lurie KG, Payen D. "Inspiratory impedance during active compression-decompression cardiopulmonary resuscitation: a randomized evaluation in patients in cardiac arrest". Circ 2000; 101(9):989-994.

Paradis, Norman A., M.D, et al.; Cardiac Arrest, the Science and Practice of Resuscitation Medicine; Second Edition, 2007, Cambridge University Press, New York.

\* cited by examiner

AUTOMATED RESUSCITATION SYSTEM INTEGRATING HEMODYNAMIC AND DEFIBRILLATORY CAPABILITIES

RELATED APPLICATIONS

This application is a continuation of co-pending U.S. patent application Ser. No. 16/514,968, filed Jul. 17, 2019, entitled INCORPORATION OF THE ELECTRODES FOR DEFIBRILLATION INTO THE PATIENT-FACING COMPONENTS OF AUTOMATED CARDIOPULMONARY RESUSCITATION SYSTEMS, which claims the benefit of U.S. Provisional Application Ser. No. 62/699,647, filed Jul. 17, 2018, entitled INCORPORATION OF THE ELECTRODES FOR DEFIBRILLATION INTO THE PATIENT-FACING COMPONENTS OF AUTOMATED CARDIOPULMONARY RESUSCITATION SYSTEMS, the entire disclosures of which are herein incorporated by reference.

FIELD OF THE INVENTION

The invention disclosed here relates in general to the field of cardiopulmonary resuscitation (CPR), and more particularly, to devices and methods for improving the clinical outcome of patients suffering cardiac arrest.

BACKGROUND OF THE INVENTION

The sudden loss of myocardial pump function, so-called cardiac arrest, is one of the leading causes of sudden death.

Since its first modern description, external chest compression based cardiopulmonary resuscitation (CPR) as a therapy for cardiac arrest has been extensively studied, and numerous refinements have been proposed. Despite this significant effort, a large majority of patients suffering sudden death will not be successfully resuscitated to discharge from the hospital capable of independent function. This is even true for patients whose cardiac arrest occurs within the hospital and who receive immediate therapy. Improving the efficacy of resuscitative treatment is one of the great unmet needs in modern medicine.

Cardiopulmonary resuscitation (CPR) may create forward blood flow by applying force to the patient's thorax either by piston type mechanisms or circumferential constriction mechanisms based on pneumatic or belt constriction. Application of suction mechanisms may allow active decompression of the chest. Addition of synchronized abdominal counterpulsation may additionally enhance the efficacy of CPR. The efficacy of active decompression CPR may be further enhanced by providing full or partial obstruction of the airway during portions of decompression so as to enhance venous return.

CPR hemodynamics may be further improved by a combination of one or more of: 1) circumferential constriction, 2) anteroposterior compression-decompression of the chest, as taught in U.S. published patent application No. 2016/0361228A1, to Norman A. Paradis, titled MECHANICAL CARDIOPULMONARY RESUSCITATION COMBINING CIRCUMFERENTIAL CONSTRICTION AND ANTEROPOSTERIOR COMPRESSION OF THE CHEST, the teachings of which are incorporated herein by reference, abdominal counterpulsation and pulsation, abdominal counterpulsation, extremity tourniqueting or pulsation, among others.

Ventricular fibrillation is one of the most common forms of cardiac arrest. It is a chaotic electrical state that precludes coordinated depolarization of the cardiac ventricles resulting in no cardiac output. It is generally treated with cardiopulmonary resuscitation (CPR) and electrical defibrillation (U.S. Pat. No. 3,093,136). Ventricular tachycardia is a clinical state in which the hearts ventricles are beating too rapidly. It may also result in clinical cardiac arrest, and its treatment may be similar to that of ventricular fibrillation.

Medical personnel refer to defibrillation with respect to a fibrillating heart, and cardioversion or countershock for termination of pulseless ventricular tachycardia. For the purposes of this disclosure, the terms "defibrillation" "shock" and "countershock" will be used interchangably with the understanding that they incorporate termination of either ventricular fibrillation or tachycardia.

Commonly, electrical countershock is performed by applying electrical potential—and thus current—across the chest via electrodes connected to a capacitor-based defibrillator. Devices for countershock are well known and consist fundamentally of an electrically charged capacitor connected to electrodes on or within the patient and a switch between the capacitor and the electrodes. (U.S. Pat. No. 3,093,136A). The electrodes on the patient were ferrous metal paddles for many years, but have now been supplanted by adhesive gel electrode pads (U.S. Pat. No. 4,539,996).

Improving the Efficacy of Electrical Countershock

The success of electrical countershock is principally associated with improved current flow across the fibrillating myocardium, which is itself a function of transthoracic resistance when using direct current. Decreasing transthoracic resistance is associated with improved current flow and techniques which lower transthoracic resistance would improve electrical countershock success. The equivalent of transthoracic resistance when using alternating current is transthoracic impedance, and measurement of transthoracic impedance with a small AC current may be used as a surrogate indicator of transthoracic resistance.

Current flow through the chest during electrical countershock may not be linear from one electrode to another, but may be nonlinear as a function of tissue and organ resistance, capacitance, or impedance. This pattern may be affected by mechanical processes such as chest compression or constriction. Air is an insulator, so the ventilatory cycle of the lungs may affect electrical countershock.

Various practitioners have described improved efficacy of defibrillation when the electrical counter shock is applied within 300 ms of chest release during CPR, as described in U.S. Pat. Nos. 8,478,401, 4,198,963, 5,626,618, and 7,186,225, the entire teachings of which are incorporated herein by reference. Esibov et al. confirmed earlier observations that varying the location of the defibrillation pads or paddles placement affects the efficacy of defibrillation. They noted that the exigencies of emergency resuscitation may interfere with optimal placement of pads.

The efficacy of electrical countershock may be significantly improved by application of multiple transthoracic pathways that are electrified near simultaneously or sequentially, as described in U.S. Pat. No. 9,174,061, the entire teachings of which are incorporated herein by reference.

The efficacy of electrical countershock may also be significantly improved by applying the countershock only when the myocardium is ready to achieve defibrillation followed by ROSC, as described in U.S. Pat. Nos. 5,571,142, and 5,957,856, the entire teachings of which are incorporated herein by reference. The state of the myocardium may be evaluated in any number of ways. In particular, Fourier transformation of the VF waveform into a power spectrum has provided predictive biomarkers.

Various practitioners have described a lowered transthoracic resistance to current flow with the application of force on defibrillation paddles—called paddle contact pressure. The transition from paddles to adhesive gel pads may actually have negatively affected this parameter as providers did not physically apply contact pressure. Various practitioners have demonstrated that applying force to the adhesive gel electrodes improved transthoracic impedance.

An association has been found between the ventilatory cycle and transthoracic impedance. They found a higher transthoracic impedance with inspiration, and a significant decrease in defibrillation success when shocks were delivered in inspiration compared to expiration.

In some studies, the performance of defibrillation is improved by using an anterior-posterior vector. In this scenario, one paddle was placed in the front of the patient, and another was placed posteriorly between the shoulder blades.

AMSA is a variation in the broad family of techniques to characterize the state of the myocardium by analysis of the electrocardiogram (ECG) ventricular fibrillation waveform. It was observed decades ago that the "coarseness" of the fibrillatory wave was associated with the likelihood of defibrillation and ROSC—the coarser the VF waveform, the better. Most of these techniques are variations of the Fourier transformation, as described in U.S. published patent application No. 2005/0245974, the entire teachings of which are encorporated herein by reference, or area-under the curve quantification of VF amplitude. For the purposes of this disclosure, these will be referred to as ECG-transforms. Persons of ordinary skill will understand that there are multiple specific types or ECG-transforms and that any may be used as an indicator or myocardial status.

It was observed decades ago that the "coarseness" of the VF wave was associated with the likelihood of defibrillation and ROSC—the coarser the VF waveform, the better. Most of these techniques are variations of the Fourier transformation (U.S. Patent No. 2005/0245974) or area-under the curve quantification of VF amplitude. There are a broad family of techniques to characterize the state of the myocardium by analysis of the ventricular fibrillation waveform. For the purposes of this disclosure, these will be referred to as "ECG-transforms." Such ECG-transforms may be used as goals or targets in resuscitation. The manner of CPR may be adjusted so as to improve this biomarker. Rescuers may choose to apply defibrillation only when the biomarker indicates that return of spontaneous circulation will occur.

In Summary, the rate of successful transthoracic defibrillation of ventricular fibrillation is increased by:

1) Applying the electrical counter shock during a specific portion of the chest compression cycle. (U.S. Pat. Nos. 8,478,401 B2 and 4,198,963 and 5,626,618 and 7,186,225).

2) Varying the location of the defibrillation pads or paddles.

3) Using multiple paths across the chest (U.S. Pat. No. 9,174,061). Such as applying two counter shocks simultaneously at a 90° angle to one another.

4) Apply force to the adhesive gel electrodes.

5) Applying the defibrillation shock only when the myocardium is ready to achieve defibrillation followed by ROSC.

5) Applying the shock at an optimal phase or airway pressure of the ventilatory cycle.

6) Apply defibrillation in an antero-postero vector and minimizing the antero-postero distance by force.

Improving the Hemodynamics of CPR

The specific mechanisms by which external chest compression achieves forward blood flow remains unclear. Two competing theories have been proposed: the cardiac pump mechanism and the thoracic pump mechanism. It is generally believed that anteroposterior compression of the sternum achieves forward blood flow principally through the cardiac pump mechanism, and that circumferential constriction CPR functions through the thoracic pump.

It has been demonstrated that, compared to classical anteroposterior compression, circumferential constriction may be associated with higher intrathoracic pressure changes, greater blood flow, and increased rates of return of spontaneous circulation. Typically, such constriction is generally achieved by inflation of a circumferential pneumatic bladder, or semi-circumferentially with a band.

The efficacy of anteroposterior compression may be improved by the addition of forceful decompression during the upstroke of the piston. Such active decompression requires attachment of the piston device to the chest. Typically, this is achieved by use of a suction cup device at the end of the piston.

The improvement in hemodynamics associated with active decompression may be mechanistically mediated by creation of increased negative intrathoracic pressure during the decompression phase of CPR, with resulting enhancement of venous return. Additional enhancement of negative intrathoracic pressure and venous return may be achieved by briefly obstructing the airway during the decompression release phase. Typically, this is achieved through utilization of a cracking valve mechanism called an impedance threshold device.

Additional interventions that may improve either circumferential constriction or anteroposterior compression of the chest include adjunctive therapy with pressor drugs, techniques that actively compress or decompress the abdomen, and techniques that synchronize components with residual cardiac function, among others. Application of a tourniquet to the extremities during CPR has been described as have the rhythmic synchronized constriction of the extremities.

Indicators of patient and myocardial status during ventricular fibrillation cardiac arrest include end-tidal CO2 (ET-CO2) and amplitude spectral area (AMSA) among others. These biomarker indicators are associated with ROSC and defibrillation success respectively. They can be used in control precision adaptive sequencing for optimization of CPR and the timing of the defibrillatory shocks.

The use of electronic systems to control the parameters of automated CPR systems has also been described in U.S. Pat. No. 9,566,210, The entire teachings of which are incorporated herein by reference.

In Summary: the efficacy of resuscitation may potentially be improved by:

1) Mechanical or pneumatic automated CPR devices, including: A) chest compression, B) chest decompression, C) chest constriction, D) abdominal Counterpulsation.

2) Methods for improving the efficacy of defibrillation, including: A) pushing on the electrodes, B) multiple current paths, C) synchronizing with ventilation, D) synchronizing with chest compressions.

However, even with these innovations having been described, a large fraction of patients suffering cardiac arrest are not successfully resuscitated. Principally, this may be because manual CPR is of only limited efficacy, and automatic mechanical systems have not had superior performance. Further improvements in the efficacy of CPR systems are urgently needed.

SUMMARY OF THE INVENTION

This present disclosure overcomes disadvantages of the prior art by providing an apparatus and system to improve the outcome of patients suffering the ventricular fibrillation or the ventricular tachycardia variants of cardiac arrest. This can be achieved by a device that fully integrates automatic mechanical or pneumatic capabilities with electrical countershock capabilities such that the probability of defibrillation or cardioversion with return of spontaneous circulation is increased.

This integrated CPR device contains a defibrillation subsystem that can be optimized both mechanically, with respect to contact pressure, and electrically with respect to both timing within the CPR cycles and electrical current flow.

The present disclosure includes a fully integrated cardiac arrest resuscitation system. The subsystems that interact with the patient to induce forward blood flow can be optimized and synchronized with the countershock subsystem to improve the success rate for defibrillation with return of spontaneous circulation (ROSC). The sequence, forces and distances of the mechanical, pneumatic, and countershock subsystems can be computer controlled. The control system may use pre-defined a priori sequences or may optimize all components based on biomarker or subsystem status feedback.

In an illustrative embodiment, an automated resuscitation system (ARS) can include at least one means for compression of the chest that produces forward blood flow, a countershock defibrillator subsystem, a plurality of countershock electrodes on patient facing portions of the ARS, and a control system that can synchronize chest compressions and countershocks. The ARS can include electrode contact enhancers. The electrode contact enhancers can be the means for compression of the chest that produces forward blood flow. The at least one means for compression of the chest can include a piston. The at least one means for compression of the chest can include bladders adapted to encircle a patient. The ARS can include a ventilation subsystem that synchronizes with the countershock defibrillator subsystem to enhance the efficacy of defibrillation. The ARS can include at least one biomarker sensor, and wherein a force of compression applied by the means for compression is dependent on a measurement from the at least one biomarker sensor. The plurality of countershock electrodes can include at least two pairs of countershock electrodes, and wherein defibrillation is achieved by multiple sequential current paths across the chest. The ARS can include a backboard, wherein at least one of the plurality of countershock electrodes is on the patient-facing surface of the backboard. At least one of the plurality of countershock electrodes can be on the patient-facing surface of the piston.

BRIEF DESCRIPTION OF THE DRAWINGS

The invention description below refers to the accompanying drawings, of which.

DETAILED DESCRIPTION

The present disclosure includes an automated resuscitation system to improve the outcome of patients suffering ventricular fibrillation or ventricular tachycardia variants of cardiac arrest. This can be achieved by a device that fully integrates automatic mechanical or pneumatic capabilities with electrical countershock capabilities such that the probability of defibrillation or cardioversion with return of spontaneous circulation is increased. For the purposes of this disclosure, the terms "defibrillation" "shock" and "countershock" will be used interchangably with the understanding that they incorporate termination of either ventricular fibrillation or tachycardia.

This integrated CPR device contains a countershock subsystem that can be optimized both mechanically, with respect to contact pressure, and electrically with respect to both timing within the CPR cycles and electrical current flow. Current flow can be enhanced by minimizing transthoracic resistance.

Figure 1:
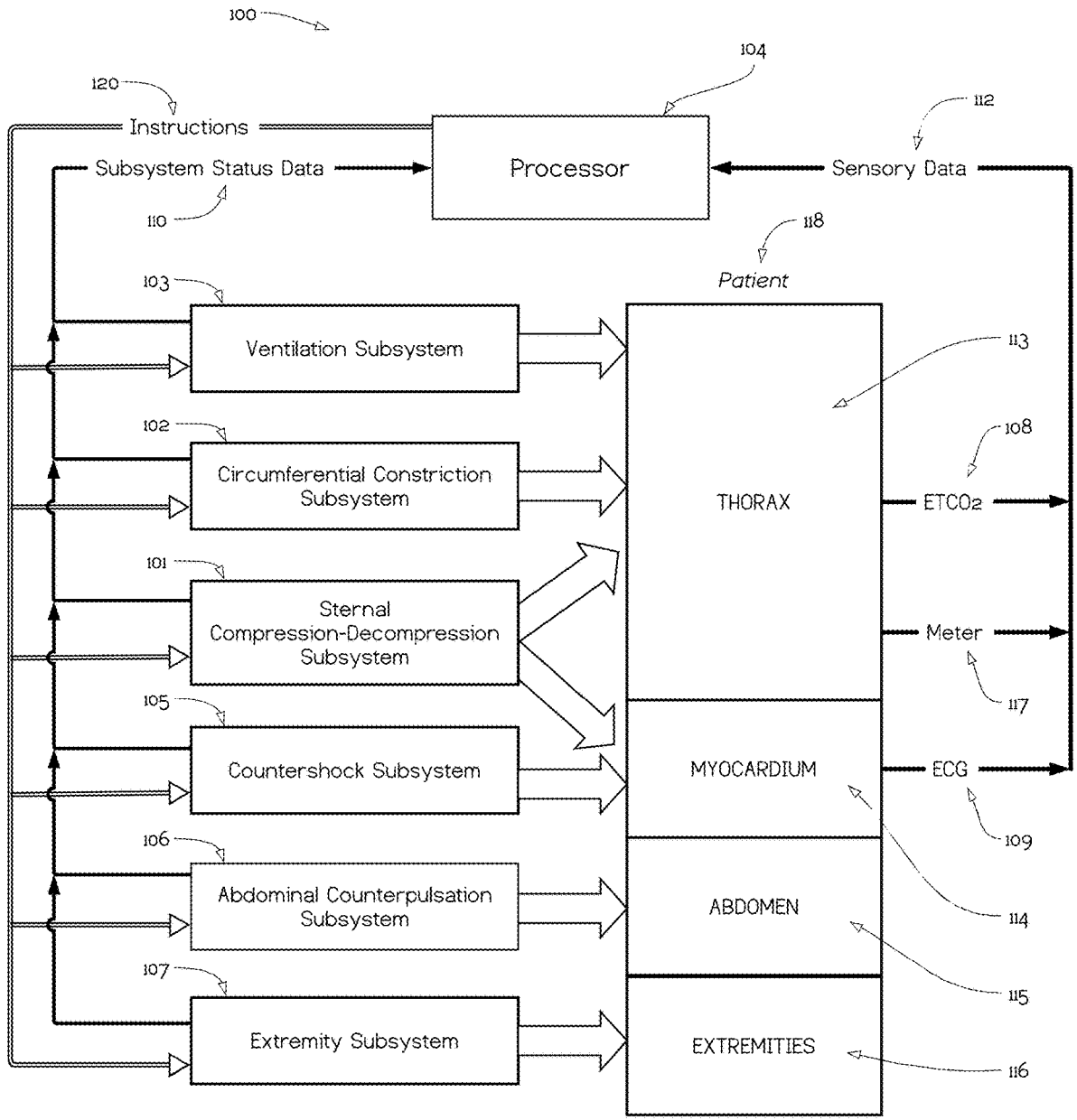
FIG. 1 is a schematic diagram of the automated resuscitation system, showing subsystem interactions with a schematic patient and the flow of subsystem and biomarker inputs and outputs, according to an illustrative embodiment.

FIG. 1 is a schematic diagram of the automated resuscitation system, showing subsystem interactions with a schematic patient and the flow of subsystem and biomarker inputs and outputs, according to an illustrative embodiment. An Automated Resuscitation System (ARS) 100 can include a controller 104, various meters, and various subsystems. The meters of the subsystem can include an end-tidal carbon dioxide (ET-$CO_2$) meter 108, an ECG 109, and/or one or more other meters 117 that can include an accelerometer, a force transducer, $SPO_2$ meter (i.e. Near-Infrared Spectroscopy (NIRS) or similar technologies), plethysmograph, and/ or an acoustical microphone. The meters of the subsystem can provide sensory data 112 to the controller 104. Subsystems of the ARS 100 can include a ventilation subsystem 103, a circumferential constriction subsystem 102, a sternal compression-decompression subsystem 101, a countershock subsystem 105, an abdominal counterpulsation subsystem 106, and an extremity subsystem 107. The various subsystems of the ARS can provide subsystem status data 110 to the controller 104.

The controller 104 can input the sensory data 112 and the subsystem status data 110, and the controller 104 can control the various subsystems based on the input data. The controller 104 can provide instructions 120 to the various subsystems. The various subsystems of the ARS can act on the patient 118, and the various meters of the ARS can collect data from the patient 118. The ventilation subsystem 103 and the circumferential constriction subsystem 102 can act on the thorax 113 of the patient. The sternal compression-decompression subsystem 101 can act on the thorax 113 and the myocardium 114 of the patient. The countershock subsystem 105 can act on the myocardium 114 of the patient. The abdominal counterpulsation subsystem 106 can act on the abdomen of the patient. The extremity subsystem 107 can act on the extremities 116 of the patient.

The subsystems of the device that interact with the patient to induce forward blood flow, including the circumferential constriction subsystem 102, the sternal compression-decompression subsystem 101, the abdominal counterpulsation subsystem 106, and/or the extremity subsystem 107, can be optimized and synchronized with the countershock subsystem 105 so as the improve the success rate for defibrillation with ROSC. The sequence, forces and distances of the various mechanical and/or pneumatic blood flow subsystems 101, 102, 106, and/or 107, and countershock subsystems 105 can be controlled by processor 104. The control system may use pre-defined a priori sequences or may optimize all components based on biomarker or subsystem status feedback, explained more fully below in regard to FIGS. 7 and 8.

The efficacy of defibrillation can be improved when the electrical countershock is applied within 300 ms of chest release during CPR. Incorporation of countershock capability within the patient-facing surface of an automated mechanical or pneumatic system can allow coordination between chest compression and the timing of defibrillation.

Figure 2A:
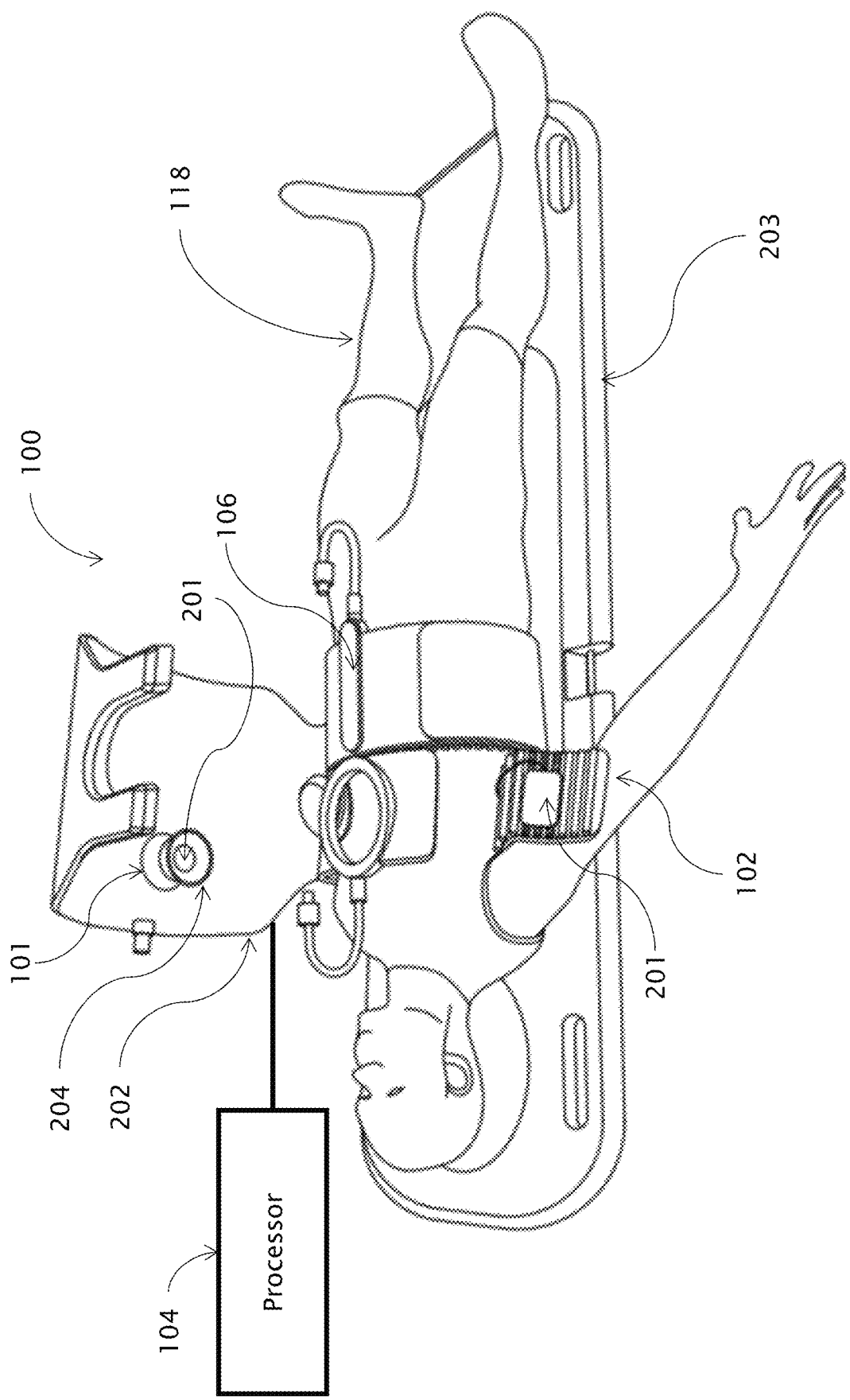
FIG. 2A is a perspective view of the automated resuscitation system in the process of being applied to a patient, according to an illustrative embodiment.

FIG. 2A is a perspective view of the automated resuscitation system in the process of being applied to a patient, according to an illustrative embodiment. An ARS 100 can have a patient-supporting backboard 203, and the ARS can include a housing 202 that can be hinged or removably connected to the backboard 203. The ARS 100 can have a controller processor 104 that can control and direct various actions, decisions, and subsystems of the ARS, and can input various measurements and data to support actions and decisions of the controller processor 104, explained more fully below. The ARS 100 can have a countershock defibrillator that can be capable of delivering a countershock to a patient. The countershock defibrillator can be integrated into the housing 202, and the controller processor 104 can control and direct the defibrillator. The ARS 100 can have a sternal compression-decompression subsystem 101 that can include a piston 204 that can provide active compression to the patient 118 and can optionally provide active decompression to the patient 118. The piston 204 can include a suction cup on the patient-facing end of the piston 204 that provide active decompression by pulling on the thorax of the patient. The ARS can have a circumferential constriction subsystem 102. Circumferential constriction subsystem 102 can include a pneumatic vest, a constricting band, and/or a series of bladders. Circumferential constriction subsystem 102 can include a plurality of bladders that can be pneumatically or hydraulically filled to provide a constricting force to the patient 118. The bladders can be a series of elongated pneumatic inflatable linear tubes that can be arranged in parallel, explained more fully below. The ARS 100 can include an abdominal counterpulsation subsystem 106 that can provide a counterpulsating force to the abdomen of the patient.

The ARS 100 can include defibrillation electrodes 201. The defibrillation electrodes 201 can be incorporated into various patient-facing components of the ARS, including the backboard 203, the circumferential constriction subsystem 102, the piston 204, and/or other patient facing components of the ARS 100. The ARS can include electrode contact enhancers. In various embodiments, the piston 204 can be an electrode contact enhancer, and the piston 204 can provide force to push the electrode against the patient. Incorporation of the countershock electrodes 201 into the patient-facing components of a comprehensive automated CPR would address the problem of suboptimal patient orientation with respect to the defibrillation electrodes. The placement of the patient within a comprehensive system would be intrinsically more reliable, providing an optimal location and orientation of the defibrillation electrodes. Multiple defibrillation electrodes 201 can be placed in various locations within the patient-facing surfaces of the ARS 100.

Multiple defibrillation electrodes 201 can be used to create multiple transthoracic pathways through the patient 118. Electric current can be directed through selected countershock electrodes 201 to create various transthoracic pathways through the patient 118. Defibrillation may be improved by application of multiple transthoracic pathways that are electrified near simultaneously or sequentially. Incorporation of the defibrillation electrodes 201 into the patient facing surfaces of the ARS 100 allows for multiple defibrillators to be discharged simultaneously or sequentially, and allows for the use of one or more transthoracic pathways between various defibrillation electrodes 201.

The defibrillation pads 201 for multiple pathways can be integrated into the patient-facing surface of an ARS system 100, and the capability of providing simultaneous or sequential multipath defibrillation can also be incorporated into the controller as an automated component. In some cases, an anterior-posterior transthoracic pathway may be optimal. The potentially optimal anterior-posterior electrode placement and current path may be utilized singly, or as part of a multi-shock simultaneous or sequential pattern.

The ARS 100 can have a controller unit with a processor 104 that can coordinate the biomarker inputs, CPR, and defibrillation functions at a speed that can be life-saving. The efficacy of defibrillation can be significantly improved by applying the defibrillation shock only when the myocardium is ready to achieve defibrillation followed by ROSC. Incorporation of the countershock and control systems into a fully automated CPR system with a controller 104 allows optimized coordination between defibrillation biomarkers and actual counter shock.

Figure 2B:
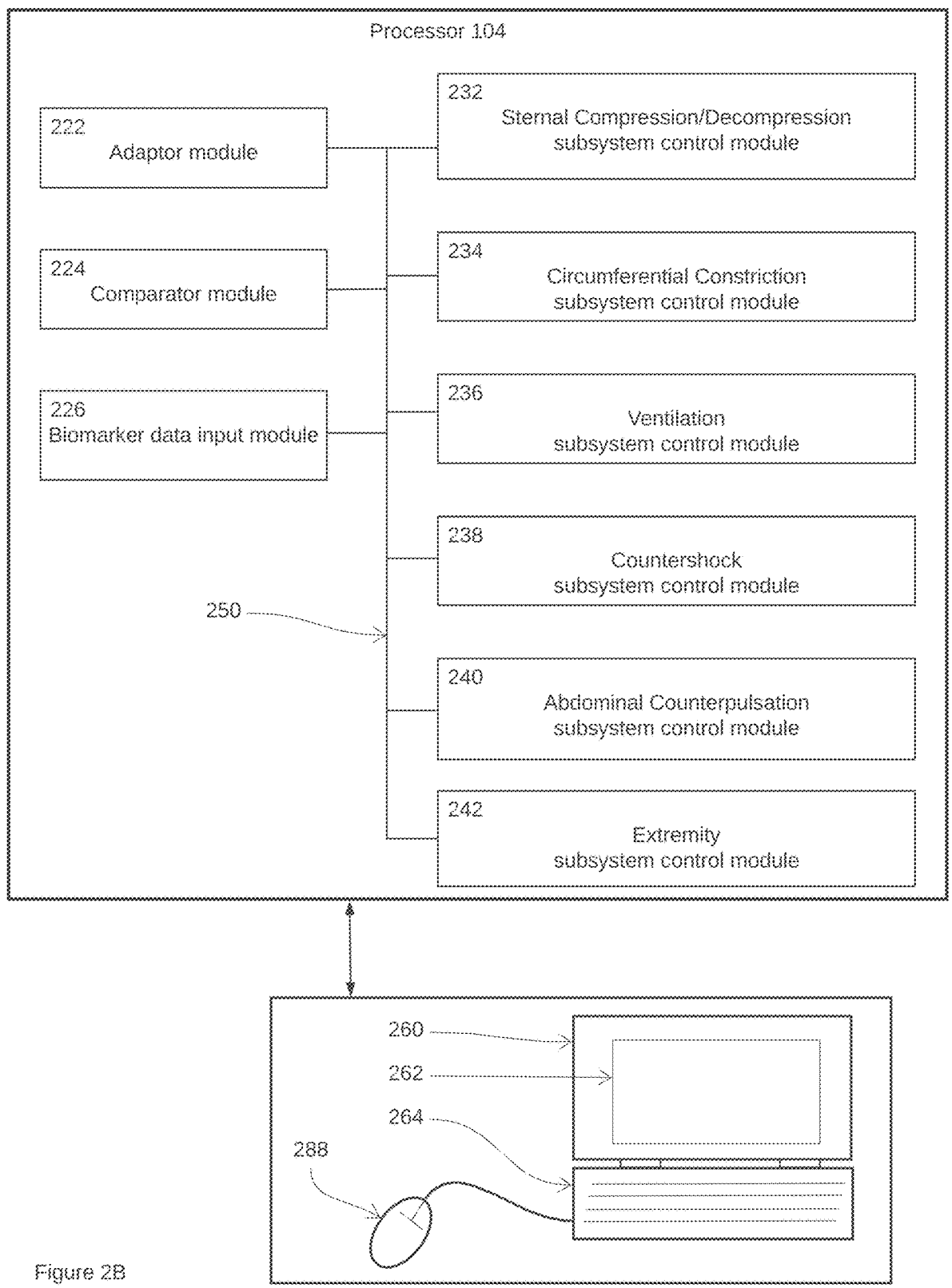
FIG. 2B is an overview of a processing and controlling system for an automated resuscitation system, according to an illustrative embodiment.

FIG. 2B is an overview of a processing and controlling system for an automated resuscitation system, according to an illustrative embodiment. An ARS can be controlled by a processor 104 that can include a plurality of modules, data inputs, and control outputs, and a user interface. The processor can be contained within a general purpose, or a dedicated, computing device 260, such as a PC, laptop, tablet or smartphone. In various embodiments, the computing device 260 can be built into, or incorporated within, the housing of the ARS. The computing device can include a user interface that can be a keyboard 264, mouse 266, touch screen or similar device, and a display 262 that can include a graphic user interface screen. In practice, a user can input instructions for a procedure through the user interface 264 into the processor 104. The programs and/or sub-programs can then process the instructions, collect measurements, and provide information to the various subsystems of the ARS.

The processor unit 104 can include a biomarker data input module 226, along with an adaptor module 222 and a comparator module 224 that can be used by the processor to optimize the performance of the ARS, explained more fully below. The processor unit 104 can include a sternum compression/decompression subsystem control module 232 that can control the functions of the sternum compression/decompression subsystem. The processor 104 can include a circumferential constriction subsystem control module 234 that can control the functions of the circumferential constriction subsystem. The processor 104 can include a ventilation subsystem control module 236 that can control the ventilation subsystem 236. The processor 104 can include a countershock subsystem control module 238 that can control the countershock subsystem. The processor 104 can include an abdominal counterpulsation subsystem control module 240 that can control the abdominal counterpulsation subsystem. The processor 104 can include an extremity subsystem control module 242 that can control the extremity subsystem.

Figure 3:
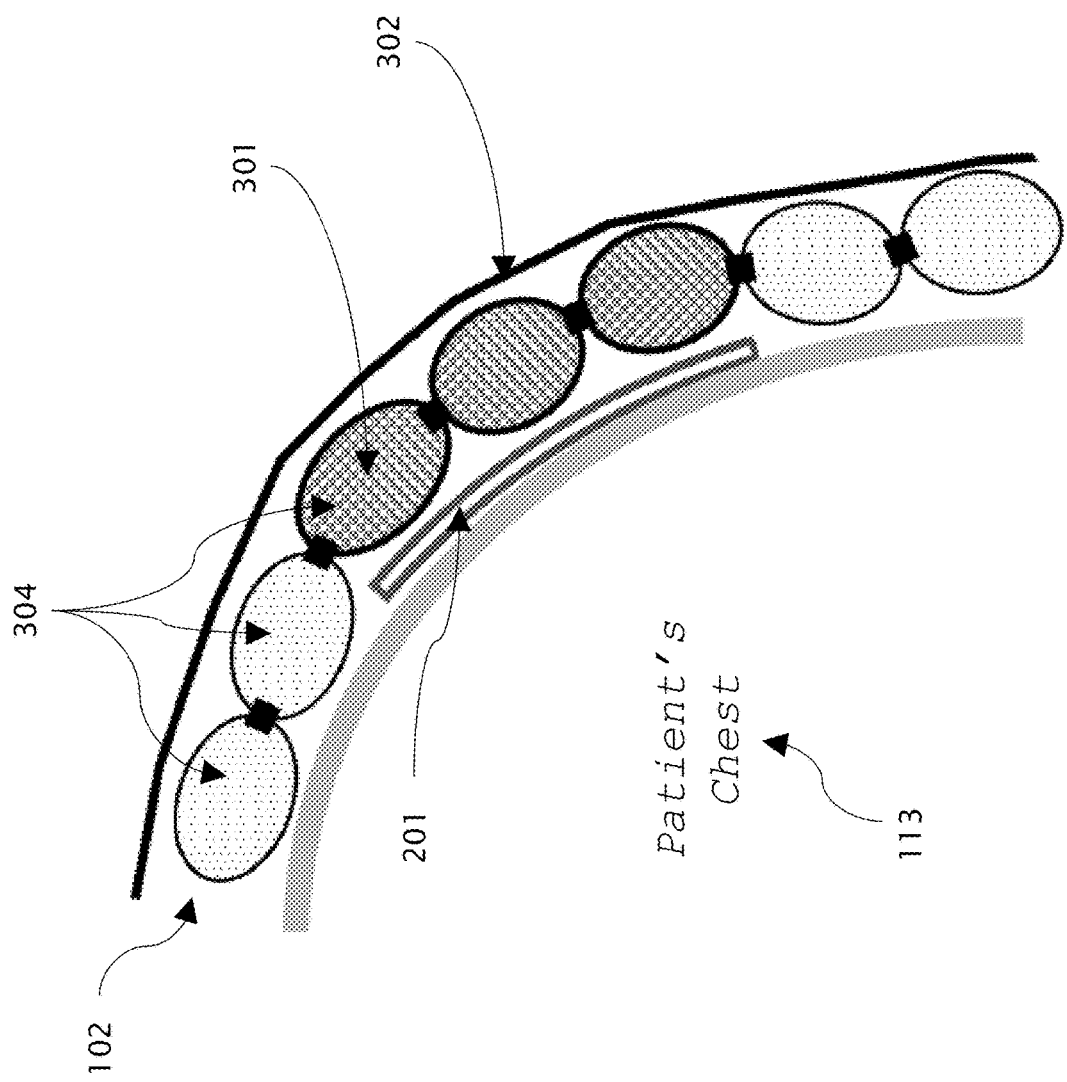
FIG. 3 is a partially cut-away view of the automated resuscitation system around a patient's thorax, showing inner workings including one of the defibrillation pads pre-installed with the circumferential constriction subsystem, according to an illustrative embodiment.

FIG. 3 is a partially cut-away view of the ARS around a patient's thorax, showing inner workings including one of the countershock electrode pads pre-installed within the circumferential constriction subsystem, according to an illustrative embodiment. The ARS 100 can include the circumferential constriction subsystem 102, and the circumferential constriction subsystem 102 can include a series of bladders 304 that can be a series of elongated pneumatic inflatable linear tubes that can be arranged in parallel around the thorax 113 of the patient. A non-distensible belt 302 can hold the bladders 304 in place around the thorax 113 of the patient. The ARS can include electrode contact enhancers. In various embodiments, the electrode contact enhancers can be pneumatic or hydraulic bladders. A subset of the bladders 304 can also be electrode contact enhancing bladders 301. Electrode pressure enhancing bladders 301 can incorporated behind the countershock electrodes 201. This subset of bladders 301 can apply force to the electrodes 201 towards the patient to enhance electrode contact pressure.

Development of adhesive gel electrodes has obviated use of force to enhance contact pressure and lower transthoracic resistance. This has created a need for devices to enhance contact pressure separate from an integrated CPR system for patients in cardiac arrest. Incorporation of electrodes into the patient facing surface of a circumferential constriction system would allow both enhanced contact pressure and ventilatory end-exhalation lung volume for optimization of transthoracic resistance and countershock success. Such a device can be used in awake or sedated patients undergoing cardioversion for atrial fibrillation.

Figure 4:
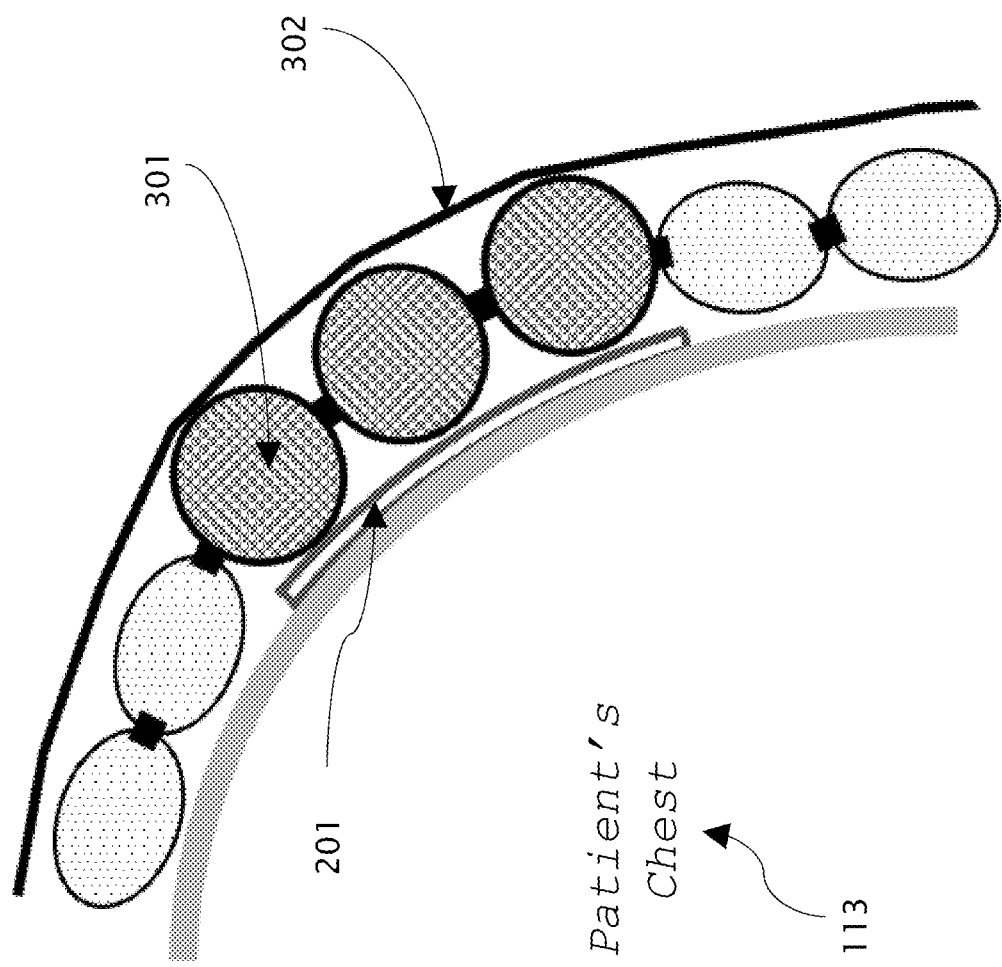
FIG. 4 is a partially cut-away view of the automated resuscitation system around a patient's thorax of FIG. 3, shown with pneumatic components selectively pushing on the defibrillation pad to improve contact pressure, according to an illustrative embodiment.

FIG. 4 is a partially cut-away view of the ARS around a patient's thorax of FIG. 3, shown with pneumatic components selectively pushing on the countershock electrode pad to improve contact pressure, according to an illustrative embodiment. The electrode pressure enhancing bladders 301 can be selectively filled to press an electrode 201 against the patient to enhance electrode contract pressure, as shown in FIG. 4.

Figure 5:
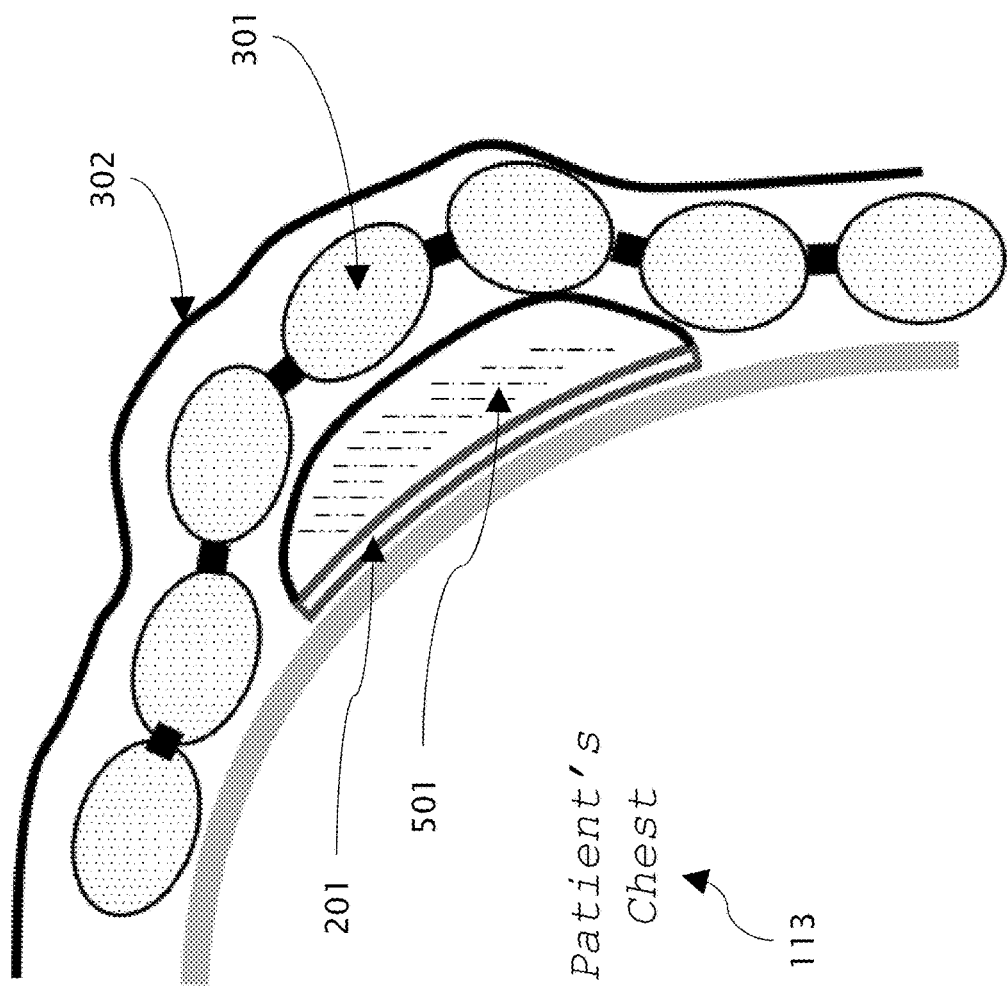
FIG. 5 is a partially cut-away view of an automated resuscitation system around a patient's thorax of FIG. 3, shown with a defibrillation electrode having an intrinsic pressure bladder, according to an illustrative embodiment.

FIG. 5 is a partially cut-away view of an automated resuscitation system around a patient's thorax of FIG. 3, shown with a countershock electrode 201 having an intrinsic pressure bladder, according to an illustrative embodiment. In various embodiments, the defibrillator electrode 201 can be affixed to an electrode pressure bladder 501. The electrode pressure bladder 501 and the defibrillator electrode 201 can be affixed to each other, and/or can be positioned with the electrode pressure bladder 501 located behind the countershock electrode 201, so that the electrode pressure bladder 501 can be inflated to provide pressure on the electrode 201. The pressure on the electrode 201 from the electrode pressure bladder 501 can press the defibrillator electrode against the patient to enhance electrode contract pressure.

Incorporation of the electrode pads into the patient-facing components of an integrated automated CPR system 201 can allow: 1) application of force to enhance electrode contact pressure, 2) synchronized and optimized application of force and countershock during the optimal interval within the chest compression cycle. Furthermore, incorporation of both the ventilatory and the countershock functions into a fully integrated automated CPR system would allow the shock to be administered during the optimal expiratory phase of ventilation. Incorporation of electrodes into the patient facing surface of a circumferential pneumatic belt can allow both enhanced contact pressure and ventilatory end-exhalation for optimization of transthoracic resistance and countershock success. Such a device can be used in awake or sedated patients undergoing cardioversion for atrial fibrillation.

Figure 6:
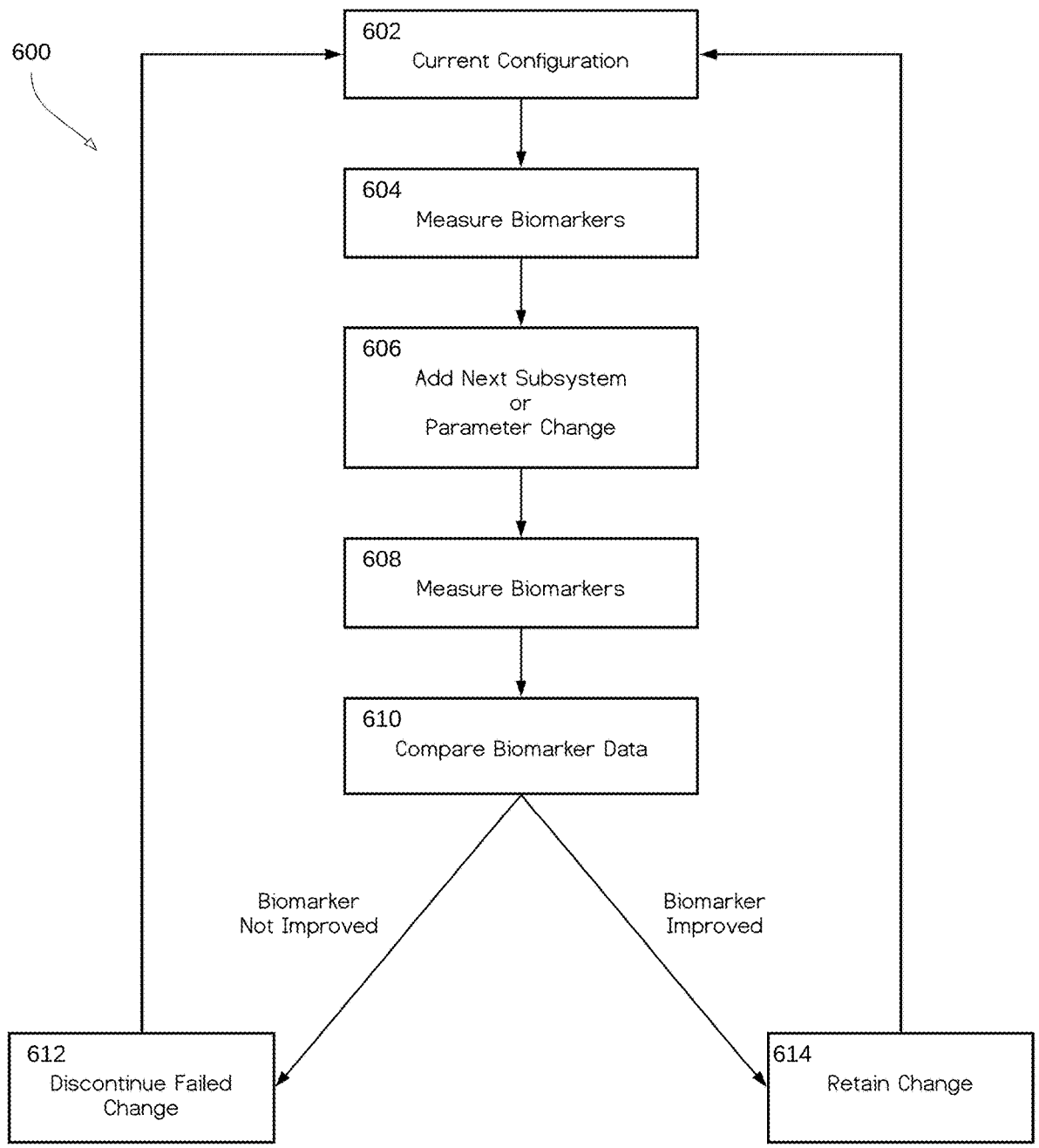
FIG. 6 is a schematic diagram of an exemplary play-the-winner heuristic sequence for adaptively optimizing the configuration of an integrated CPR system, according to an illustrative embodiment.

FIG. 6 is a schematic diagram of an exemplary play-the-winner heuristic sequence for adaptively optimizing the configuration of an integrated CPR system, according to an illustrative embodiment. The play-the-winner heuristic process 600 allows the processor to optimize the parameters for the ARS. At 602, the processor starts with the current CPR parameters, and the processor directs the ARS to operate using the current parameters. At 604, the one or more meters of the ARS measure one or more biomarkers, and the meters provide the data as an input to the processor. At 606, the adjustor module of the processor adjusts, adds, or changes a parameter for the ARS, explained more fully below, and the processor directs the ARS to operate using the changed parameters. At 608, the one or more meters of the ARS measure the same one or more biomarkers that were measured at 604, and the measured data is provided as an input to the processor. At 610, the comparator module of the processor compares the biomarker data measured at 604 before the adjustment to the biomarker data measured at 608 after the adjustment, and the comparator module determines, based on the measured biomarker data, whether the ARS was more effective before the adjustment or after the adjustment.

If the biomarker data is not improved after the change, the failed change is discontinued at 612, and the process returns to the previous current configuration at 602, or proceeds directly to testing a new parameter change at 606. If the biomarker data is improved after the change, the successful change is retained at 614, and the changed parameter becomes part of the current configuration. When the successful change is retained at 614 and it becomes part of the adjusted parameters, the process 600 can return to 602, or the process 600 can return to 606 where another new adjustment or change to the parameters is applied. The heuristic process 600 can include repeatedly cycling through the heuristic process, applying various different parameter changes (described more fully below) and comparing the new biomarker data to the previous biomarker data to determine the optimal parameters.

Figure 7:
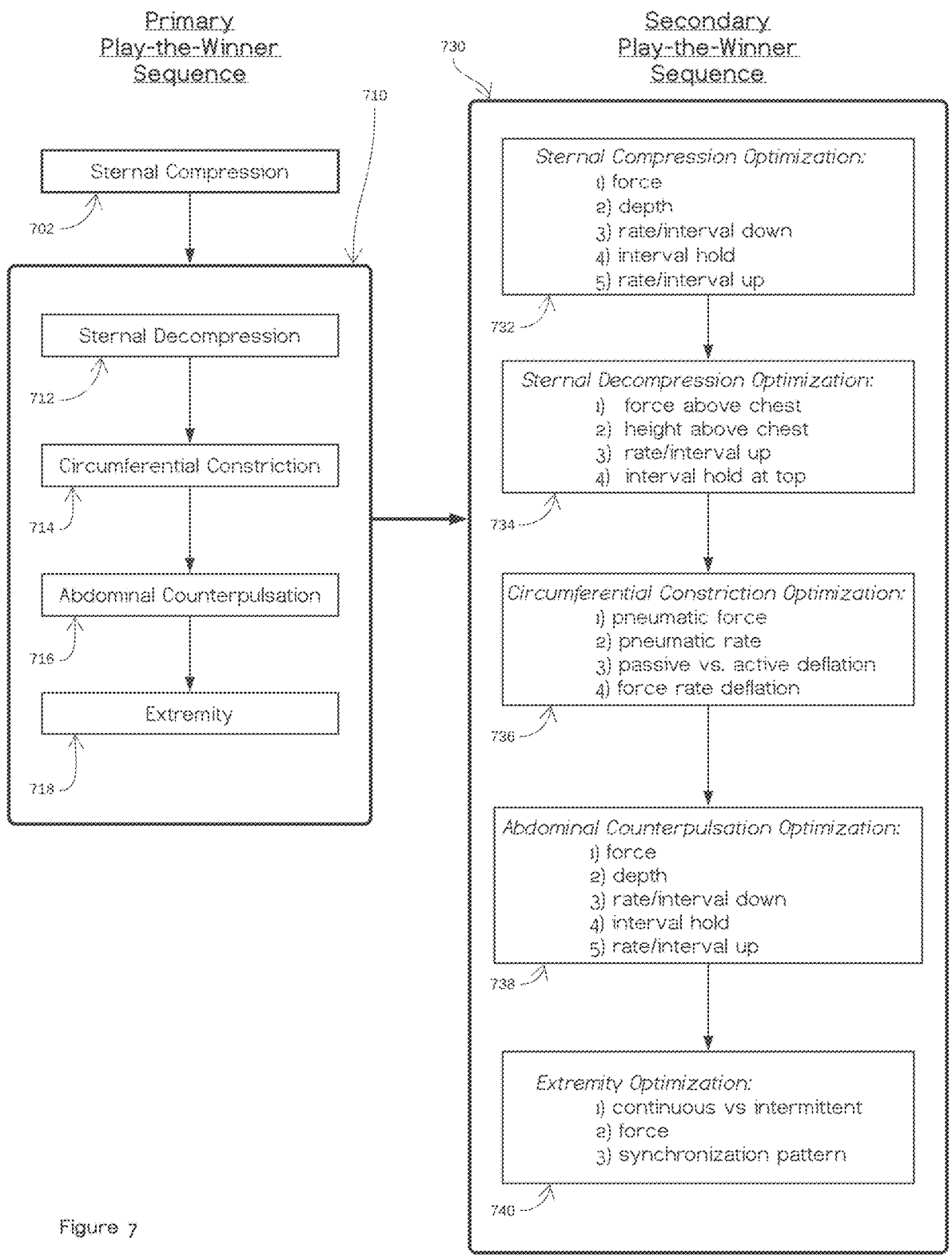
FIG. 7 is a flow diagram of exemplary primary and secondary sequences for adaptively optimizing an integrated CPR system, according to an illustrative embodiment.

FIG. 7 is a flow diagram of exemplary primary and secondary sequences for adaptively optimizing an integrated CPR system, according to an illustrative embodiment. The play the winner system 700 can include a primary sequence 710 and a secondary sequence 730. In the primary sequence 710, the processor uses a play-the-winner heuristic 600 to include or exclude each of the major effector subsystems in turn. After the primary play-the-winner sequence has determined which subsystems will be used, the secondary play-the-winner sequence 730 optimizes the performance parameters of those selected subsystems that remain in the configuration at the end of the primary sequence.

At 702, CPR can be started with standard sternal compression only, and at standard force-depth parameters. After the initiation of standard sternal compression, the processor can initiate the primary effector subsystem optimization sequence 710. Based on biomarker feedback and the play-the-winner heuristic 600 of FIG. 6, the processor can add and evaluate sternal decompression, circumferential constriction, abdominal counterpulsation, and extremity augmentation in turn and a subsystem in/out decision can be made by the processor with respect to each. At 712, the adjuster module can add sternum decompression to the ARS, and the comparator module can evaluate whether sternal decompression leads to improved biomarkers, and then the processor can include or remove sternal decompression from the ARS parameters. At 714, the adjuster module can add circumferential constriction to the ARS, and the comparator module can evaluate whether circumferential constriction leads to improved biomarkers, and then the processor can include or remove circumferential constriction from the ARS parameters. Because this sequence is initiated with sternal compression at 702, the in/out decision for sternal compression cannot be initiated until after circumferential constriction evaluation 714. In the subset of patients in whom circumferential constriction is found to be biomarker enhancing, the utility of sternal compression can then be evaluated using the play-the-winner heuristic 600. In the other subset of patients—those whose biomarkers do not improve with circumferential constriction, sternal compression alone can be retained as the sole thoracic subsystem.

At 716, the adjuster module can add abdominal counterpulsation to the ARS, and the comparator module can evaluate whether abdominal counterpulsation leads to improved biomarkers, and then the processor can include or remove abdominal counterpulsation from the ARS parameters. At 718, the adjuster module can add extremity constriction to the ARS, and the comparator module can evaluate whether extremity constriction leads to improved biomarkers, and then the processor can include or remove extremity constriction from the ARS parameters. In various embodiments, all or less than all, of the various subsystems may be included in the ARS and may be tested using the primary play the winner system 710 and the heuristic 600. In various embodiments, the order in which the various subsystems are added and tested can be varied.

At the end of the primary sequence 710, the system moves on to the secondary sequence 720 and each subsystem can be optimized in turn using the heuristic 600 of FIG. 6. If sternal compression is retained after the primary optimization sequence 710, it may be optimized at 732 using heuristic 600 in the secondary sequence 730. The sternal compression optimization 732 can include adjusting and optimizing various parameters including force, depth, rate/interval down, interval hold, rate/interval up, among other parameters and characteristics of pistons pushing on objects. The comparator module can evaluate whether the one or more adjustments made at 732 by the adjustor module lead to improved biomarkers, and then the processor can include or remove the adjusted parameters from the current parameter configuration of the ARS using the heuristic 600.

If sternal decompression is retained after the primary optimization sequence 710, it may be optimized at 734 using heuristic 600 in the secondary sequence 730. The sternal decompression optimization 734 can include adjusting and optimizing various parameters including force above chest, height above chest, rate/interval up, interval hold at top, among other parameters and characteristics of pistons pulling on objects. The comparator module can evaluate whether the one or more adjustments made at 734 by the adjustor module lead to improved biomarkers, and then the processor can include or remove the adjusted parameters from the current parameter configuration of the ARS using the heuristic 600.

If circumferential thoracic constriction is retained after the primary optimization sequence 710, it may be optimized at 736 using heuristic 600 in the secondary sequence 730. The circumferential thoracic constriction optimization 736 can include adjusting and optimizing various parameters including pneumatic force, pneumatic rate, passive versus active deflation, and forceful deflation, among other parameters and characteristics of belts and bladders constricting objects. The comparator module can evaluate whether the one or more adjustments made at 736 by the adjustor module lead to improved biomarkers, and then the processor can include or remove the adjusted parameters from the current parameter configuration of the ARS using the heuristic 600.

If abdominal counterpulsation is retained after the primary optimization sequence 710, it may be optimized at 738 using heuristic 600 in the secondary sequence 730. The abdominal counterpulsation optimization 738 can include adjusting and optimizing various parameters including force, depth, rate/interval down, interval hold, rate interval up among other parameters and characteristics of bladders or pistons pushing on objects. The comparator module can evaluate whether the one or more adjustments made at 738 by the adjustor module lead to improved biomarkers, and then the processor can include or remove the adjusted parameters from the current parameter configuration of the ARS using the heuristic 600.

If extremity constriction is retained after the primary optimization sequence 710, it may be optimized at 740 using heuristic 600 in the secondary sequence 730. The extremity constriction optimization 740 can include adjusting and optimizing various parameters including continuous versus intermittent constriction, force, and synchronization pattern among other parameters and characteristics of belts and bladders constricting objects. The comparator module can evaluate whether the one or more adjustments made at 740 by the adjustor module lead to improved biomarkers, and then the processor can include or remove the adjusted parameters from the current parameter configuration of the ARS using the heuristic 600.

In various embodiments, all or less than all, of the various subsystems may be included in the ARS and may be tested using the secondary play the winner system 730 and the heuristic 600. In various embodiments, the order in which the various subsystems are added and tested can be varied. In various embodiments, the processor can fully optimize each subsystem before moving on to the next subsystem. In various embodiments, the processor can gradually optimize various subsystems in parallel. In various embodiments, the secondary play-the-winner system can determine that an optimal set of parameters has been reached and then can discontinue or temporarily discontinue the optimization. In various embodiments, the secondary play-the-winner system can continue to perform the optimizations of FIG. 7 using the heuristic of FIG. 6 indefinitely.

Figure 8:
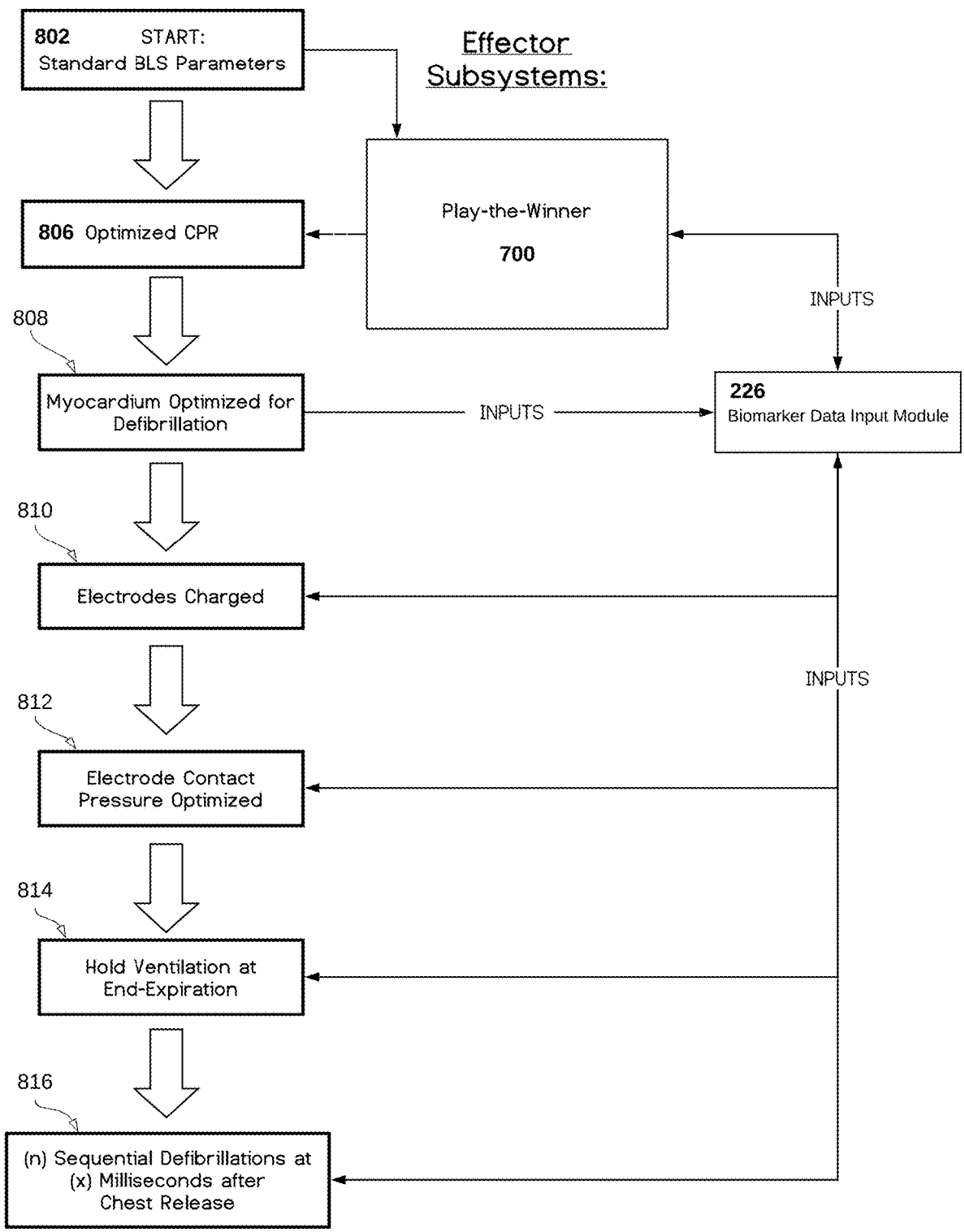
FIG. 8 is a flow diagram of an exemplary clinical process demonstrating an integrated sequence of all ARS subsystems so as to enhance defibrillation, according to an illustrative embodiment.

FIG. 8 is a flow diagram of an exemplary clinical process demonstrating an integrated sequence of all ARS subsystems so as to enhance defibrillation, according to an illustrative embodiment. At 802, the controller can direct the process to begin with the standard sternal compressions derived from current American heart Association guidelines. In 2017, the guidelines suggested a compression depth of at least 5 cm in 70 kg adults and a rate of 100 compressions per minute. This can result in a compression-decompression cycle time of 600 milliseconds for each cycle. At a 50% duty cycle, this is 300 ms compression phase and 300 ms decompression phase.

At 700, the controller can initiate the effector subsystem optimization process of FIG. 7 using the heuristic process 600 of FIG. 6, as explained above in regard to FIGS. 6 and 7. This adaptive optimization process with the mechanical-pneumatic subsystems allows the processor to incorporate substantial optimizations and improvements into the ARS system. The processor can begin to optimize the parameters using the baseline measurement of ET-CO2 levels from ET-CO2 meter and ECG derived biomarkers from ECG, along with any other meters included in the system. Then, based on the play-the-winner sequence described in FIGS. 6 and 7, the effector subsystem optimization at 700 can include the primary play-the-winner sequence determining the inclusion or exclusion of whole effector subsystems based on standard parameters. The secondary play-the-winner sequence optimizes those effector subsystems that remain at the end of the primary sequence.

If sternal compression is retained at 700 after the primary optimization sequence, it may be optimized in the secondary sequence with respect to force, depth, rate/interval down, interval hold, rate/interval up, among other parameters and characteristics of pistons pushing on objects.

If sternal decompression is retained at 700 after the primary optimization sequence, it may be optimized in the secondary sequence with respect to force above chest, height above chest, rate/interval up, interval hold at top, among other parameters and characteristics of pistons pulling on objects. By way of example, active decompression of the sternum may achieve an anterior displacement of 10% greater than the starting anteroposterior diameter. In normal-sized adults, 200-400 N of force may be required to achieve this displacement.

If circumferential thoracic constriction is retained at 700 after the primary optimization sequence, it may be optimized in the secondary sequence with respect to pneumatic force, pneumatic rate, passive versus active deflation, and forceful deflation, among other parameters and characteristics of belts and bladders constricting objects. By way of example, circumferential pneumatic thoracic constriction may be performed simultaneous with each sternal compression, and with pneumatic pressures would be between 180 and 250 mm Hg.

If abdominal counterpulsation is retained at 700 after the primary optimization sequence, it may be optimized in the secondary sequence with respect to force, depth, rate/interval down, interval hold, rate interval up among other parameters and characteristics of bladders or pistons pushing on objects. By way of example, anterior abdominal pneumatic counterpulsation may occur during the 300 ms relaxation phases of the chest compression-constriction cycle. This may be achieved with a pneumatic bladder or series of bladders cyclically inflated to pressures 180- and 250-mm Hg. and constrained within a non-dispensable belt 302.

If extremity optimization is retained at 700 after the primary optimization sequence, it may be optimized in the secondary sequence with respect to continuous versus intermittent constriction, force, and synchronization pattern among other parameters and characteristics of belts and bladders constricting objects. By way of example, extremity counterpulsation may be via pneumatic constriction during the relaxation phase of the thoracic subsystems, and with pneumatic pressures would be between 180 and 250 mm Hg.

At 806, CPR optimized with respect to its subsystems at 700 can then be applied, possibly along with adjunctive therapies, until organ measurements such as ECG-AMSA indicate that the myocardium is in a state associated with likely ROSC.

At 808, the processor can determine when the measurements indicate that the oxygen and energetic state of the myocardium had improved to a level sufficient for defibrillation with ROSC. These data measurements can be inputs to the controller subsystem. When the processor determines that the myocardium has improved to a level sufficient for defibrillation with ROSC, the processor can proceed to 810.

At 810, the countershock subsystem 105 can charge the electrodes.

At 812, the contact pressure subsystem can pneumatically or mechanically apply pressure to the electrodes.

At 814, the ventilation subsystem can discontinue ventilation at the end of the expiration.

At 816, the countershock subsystem can apply standard or alternative countershock (i.e. simultaneous or sequential) at a predetermined time that can be just after release of chest compression and constriction. In various embodiments the countershock subsystem can apply standard or alternative countershock during the 200 ms just after release of chest compression and constriction. In various embodiments, the countershocks can be single, simultaneous, or sequential, and can be provided through one or more various transthoracic pathways.

Each subsystem within this illustrative sequence can provide feedback inputs to the controller.

If countershock did not result in return of spontaneous circulation, the sequence could be repeated or iteratively adapted based on further permutations in play-the-winner heuristic sequences.

Figure 9:
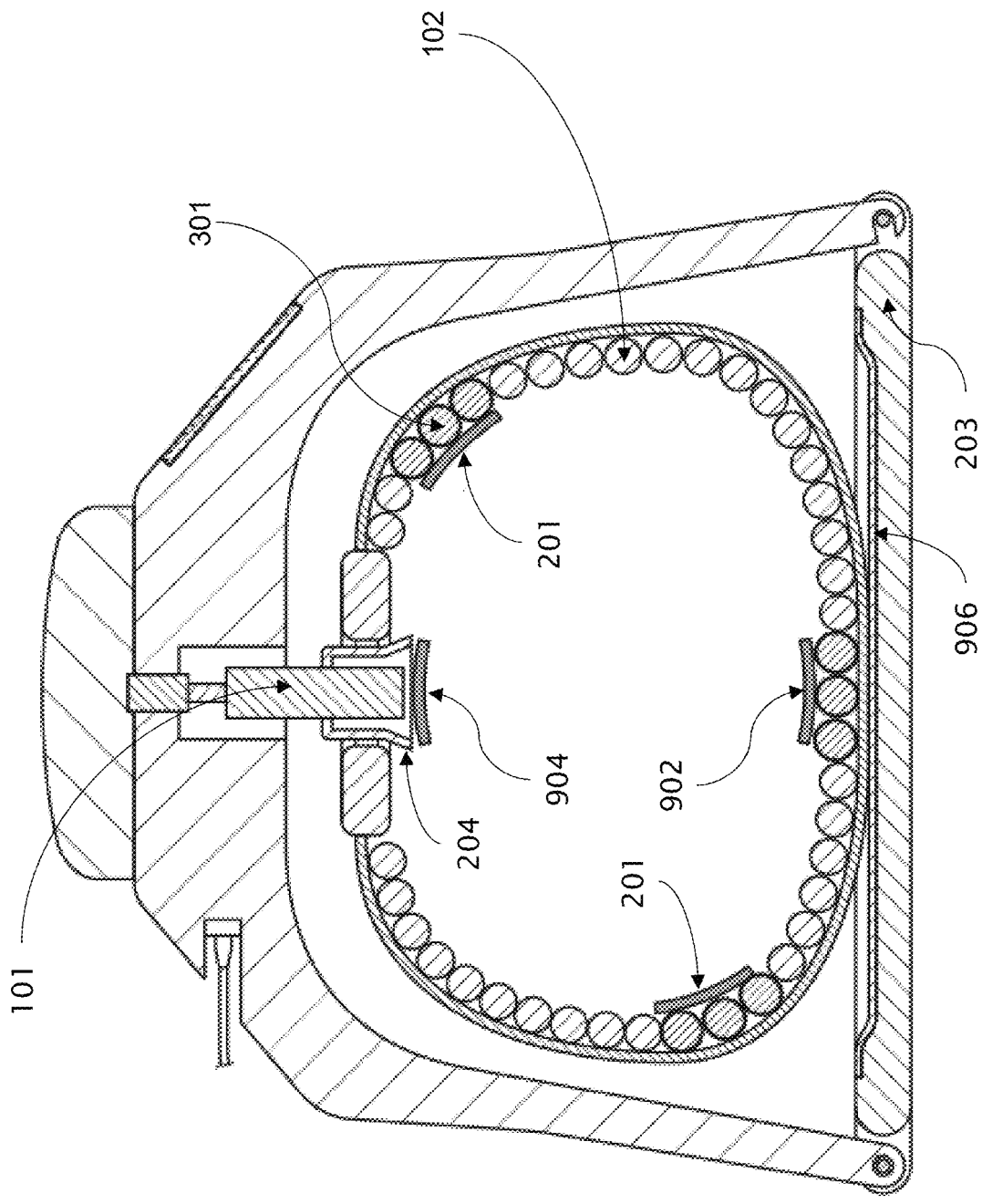
FIG. 9 is a partially cut-away view of a thoracic compression-decompression subsystem of the automated resuscitation system, according to an illustrative embodiment.

FIG. 9 is a partially cut-away view of a thoracic compression-decompression subsystem and constriction subsystem of the ARS, according to an illustrative embodiment. An ARS 100 can have multiple pairs of countershock electrodes 201, and the electrodes 201, 904, 906 can have various hydraulic, pneumatic, or mechanical means for providing force on the electrode 201 against the patient. As shown in FIG. 9, the first electrodes 201 have pneumatic bladders 301 behind them to provide force on the electrodes 201. In various embodiments, the ARS 100 can have one pair of countershock electrodes, or can have more than two countershock electrodes, and in various embodiments the ARS 100 can have four or more countershock electrodes. In various embodiments, the ARS 100 can have a pair of electrodes 902 and 904 positioned to apply posterior-anterior countershocks. The ARS can include a pneumatic or hydraulic bladder 906 in the backboard 203, and the bladder

906 can provide additional force to push upward, enhancing CPR and defibrillation. The backboard bladder 906 can push upwards on the patient to enhance CPR outcomes, and/or can be used to provide force pushing the electrode against the patient to enhance defibrillation outcome. The upper defibrillator electrode 904 can be positioned on the piston 204, so that the piston 204 can provide force on the upper defibrillator electrode 904 against the patient to provide contact pressure and improve the defibrillation outcome.

In some situations, the defibrillation vectors of anterior to posterior or posterior to anterior between defibrillator electrodes 904 and 906 can be a superior transthoracic pathway, and the present device can allow for use of this optimal pathway. This current pathway can potentially be used singly, but can also be incorporated in dual/double sequential/simultaneous defibrillation. Resuscitation is often performed with the patient in a supine position, so it can be difficult to place the posterior countershock electrode. Incorporation of the defibrillatory functions into a fully integrated automated CPR system causes the posterior electrode to be automatically in contact with the patient when the patient is placed in the ARS 100 system. Incorporation of the defibrillatory functions into a fully integrated automated CPR system also allows the countershock to be administered anterior to posterior or vice versa, and alone or in coordination with another countershock pathway. The countershocks can be delivered through multiple different transthoracic pathways, and shocks along different transthoracic pathways can be delivered sequentially or simultaneously.

Figure 10:
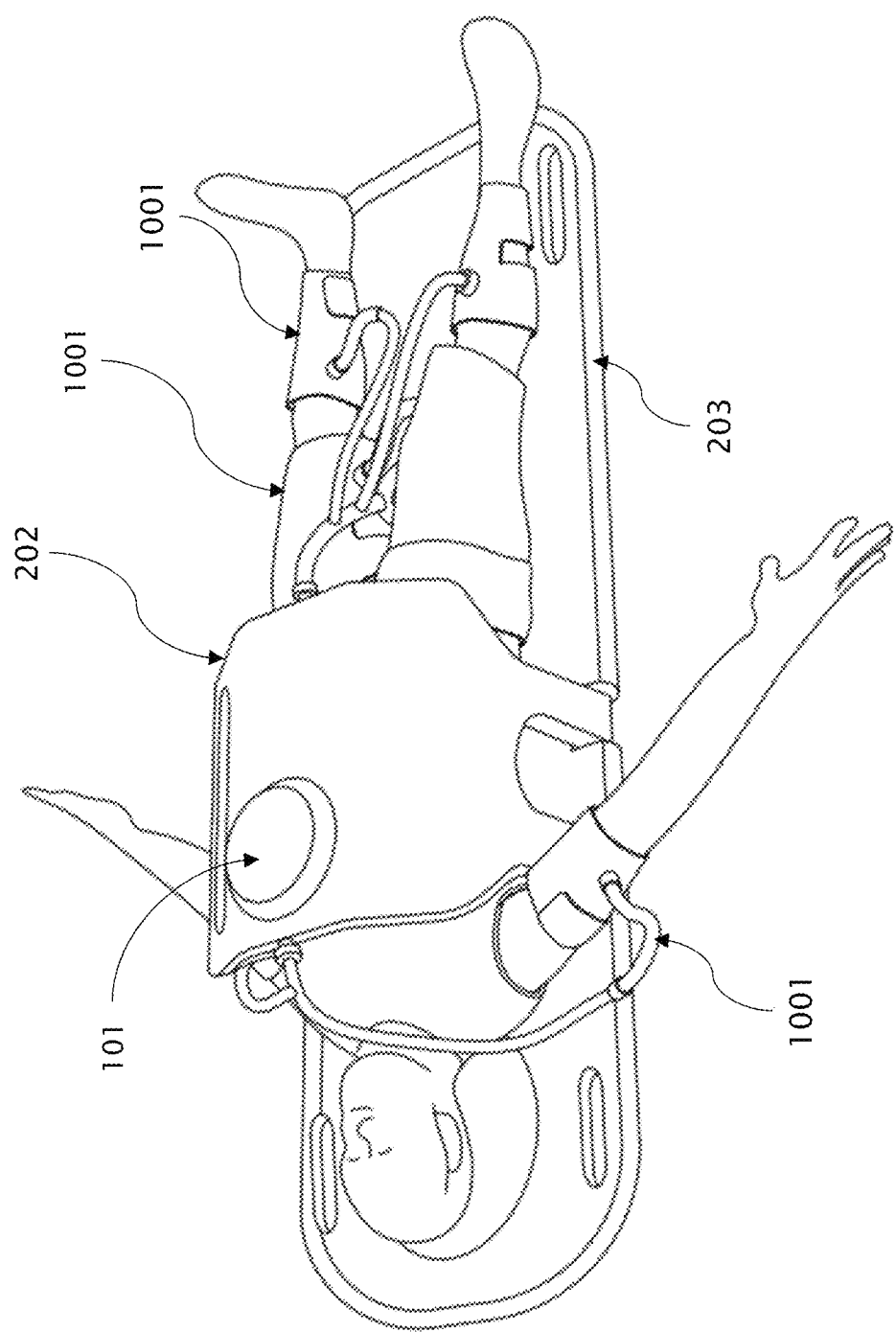
FIG. 10 is a perspective view of the automated resuscitation system including an extremity subsystem, according to an illustrative embodiment.

FIG. 10 is a perspective view of the automated resuscitation system including an extremity subsystem, according to an illustrative embodiment. An ARS 100 can have a backboard 203 and a housing 202. The ARS 100 can include a sternal compression/decompression system 101 that can be a piston. The ARS system can include extremity constrictors 1001. The extremity constrictors 1001 can be bands, bladders, or straps that can be wrapped around the patient's limbs, and the limb constrictors 1001 can be hydraulically or pneumatically powered, so that the hydraulic or pneumatic force can cause the constrictors to constrict around the patient's limbs. The constrictors 1001 can act similar to a tourniquet, and can squeeze the blood towards the thorax of the patient. In various embodiments, multiple constrictors 1001 can be used in series, with a first set of constrictors at the ends of the limbs can squeeze first, followed by a next set of constrictors closer to the thorax that can continue to squeeze blood closer to the thorax.

In various embodiments, the processor controlling the timing of defibrillation can apply the electrical countershock during one or more specific portions of the chest compression or constriction cycle. In various embodiments, the processor controlling the timing of defibrillation can apply the current for electrical countershock to varying patterns of electrodes as a function of measured impedance, resistance, capacitance, indicators of tissue perfusion, the amplitude of the ventricular fibrillation, the median frequency of the ventricular fibrillation, and/or the power spectra of the ventricular fibrillation. In various embodiments, the processor controlling the defibrillation can apply the current for electrical countershock to differing combinations of electrodes such that multiple paths across the chest can be utilized simultaneously or in sequence. In various embodiments, the processor controlling the timing of defibrillation can apply the current for electrical countershock to combinations of electrodes so that two countershocks at an angle to one another can be applied simultaneously. In various embodiments, the processor controlling the defibrillation can apply the current for electrical countershock to a series of electrodes such that the pathway of current flow through the chest can start in one or more vectors and can transition into a different set of vectors. In various embodiments, the mechanical, pneumatic, or hydraulic components can vary the force or pattern of chest compression or constriction so as to enhance the efficacy of defibrillation. In various embodiments, the mechanical, pneumatic, or hydraulic components can vary the force or pattern of chest compression or constrictions so as to apply force selectively to the electrodes at the time of their defibrillatory discharge. In various embodiments, the electrodes can be incorporated into various surfaces, including the patient facing surfaces of the piston, the suction cup, the backboard, struts on either side of the patient's thorax intended for stabilization, pneumatic or hydraulic bladders, pneumatic or hydraulic vests, constricting belts, the backboard, or a pneumatic or hydraulic bladder between the patient and the backboard. In various embodiments, the processor can receive measurement data from one or more of thoracic resistance, capacitance, impedance, and/or current flow. In various embodiments, the force, location or timing parameters of chest compression or constriction are adjusted so as to optimize one or more of thoracic resistance, capacitance, impedance, or current flow. In various embodiments, the pattern of synchronized ventilation can be adjusted so as to optimize one or more of thoracic resistance, capacitance, impedance, and/or current flow. In various embodiments, the electrodes can be removable and disposable. In various embodiments, the permanent patient-facing components can be designed for insertion of electrodes that are removable and disposable. In various embodiments, the sensory signals can be input into the processor for the purpose of optimization and/or synchronization of mechanical CPR or electrical defibrillation, and may originate from one or more of: an electrocardiogram, an accelerometer, a force transducer, ET-CO2, SPO2, an acoustical microphone or the mechanical or electrical subsystems. In various embodiments, the ARS can include a mechanical or pneumatic component for continuous or intermittent compression of the abdomen. In various embodiments, the ARS can include an esophageal defibrillation electrode. In various embodiments, the ARS can include a mechanical or pneumatic component for continuous or intermittent compression of the abdomen with one or more electrodes on its patient-facing surface.

Various embodiments described herein can include installing and integrating the defibrillation subsystem into a multimodal automatic CPR system capable of one or more of thoracic compression/decompression/constriction, abdominal counterpulsation, ventilation, and limb constriction.

Various embodiments described herein can include a multimodal CPR system whose subsystems may include one or more from a list including: sternal compression and decompression, thoracic circumferential constriction, abdominal pulsation and counterpulsation, extremity tourniquet or counterpulsation.

Various embodiments described herein can include utilizing the mechanical or pneumatic capabilities of a manual or automatic CPR to enhance the efficacy of the defibrillation system.

Various embodiments described herein can include utilizing the ventilatory subsystem of an automatic CPR to enhance the efficacy of the defibrillation system.

Various embodiments described herein can include utilizing the processor and control system of an automatic CPR device to enhance the efficacy of the countershock system.

Various embodiments described herein can include utilizing the thoracic components along with the processor of a multimodal automatic CPR system to selectively optimize the defibrillation electrode contact pressure.

Various embodiments described herein can include utilizing the processor of a multimodal automatic CPR system to optimize the countershock timing with respect to the chest compression-decompression and constriction-relation cycles.

Various embodiments described herein can include utilizing the ventilation subsystem and processor of a multimodal automatic CPR system to optimize the lung inflation such that countershock occurs at end-expiration lung volume.

Various embodiments described herein can include utilizing multiple subsystems of a multimodal automatic CPR system to provide countershock optimized with respect to contact pressure, CPR cycle and ventilation cycle.

Various embodiments described herein can include incorporating a dual/triple/(N) sequential or simultaneous defibrillation capability into a multimodal automatic CPR system.

Various embodiments described herein can include utilizing multiple subsystems of a multimodal automatic CPR system to provide dual/triple/(N) sequential or simultaneous defibrillation optimized with respect to contact pressure, CPR cycle and ventilation cycle.

Various embodiments described herein can include a precision adaptive sequence for a multimodal automatic CPR system in which the decision inputs can be ET-$CO_2$ for hemodynamics or an AMSA-like transformation of the fibrillation ECG.

Various embodiments described herein can include a precision adaptive sequence for a multimodal automatic CPR system including a play-the-winner heuristic in which the current configuration is chosen adaptively based on the biomarkers as the decision input.

Various embodiments described herein include allowing the change from baseline itself to be used as a biomarker indicative of patient or myocardial status in cardiac arrest, and that biomarker can be used for rapid decision support by the control subsystem of a multimodal automatic CPR system.

Within the context of the invention disclosed herein, the term countershock subsystem has a significantly expanded spectrum of capabilities. It can do more than simply charge the electrodes and release current from the storage capacitors. It can further interface with the processor, providing status data to the controller and receiving instructions from the controller. It can countershock via multiple positive-negative defibrillation electrode pairs. Upon receiving a countershock instruction the controller countershock subsystem can activate selective pneumatic or mechanical adjuncts, described above, to increase electrode contact pressure. It can then provide electrical countershock that may be single, dual simultaneous/sequential, or N simultaneous/sequential, which can be two or more simultaneous/sequential countershocks. One of the electrode pairs may include a positive or negative electrode within the esophagus.

The patient-facing components for electrical countershock, such as adhesive gel electrodes, and the associated electronics such as the processor may be fully incorporated into the housing of an automated mechanical/pneumatic CPR system. Alternatively, one or more of the subsystems may be housed separately from the main device. In the case of the countershock subsystem, it may be housed separately and connected to the main device by electrical cables. A system integrating multiple hemodynamic enhancements with defibrillation enhancements may, at any given moment, only be applying a subset of its multiple modalities.

Subsystems that interact with the patient mechanically, pneumatically or kinetically to induce or enhance forward blood flow may be one or more selected from the group consisting of: thoracic anteropostero compression; thoracic anteropostero decompression; thoracic constriction; abdominal counterpulsation and pulsation; abdominal cuadad to cepholad rhythmic compression; a pneumatic inflatable bladder under either the chest and/or abdomen; tourniqueting the extremities, either continuously, or on an interrupted basis; compressing or decompressing the extremities, either in a pulsation or counterpulsation pattern, either passively or actively, assisted head-up patient positioning, either the whole backboard or a hinged upper section; and/or esophageal balloon inflation or synchronized pulsation.

Pneumatic systems may apply force to the patient for creation of forward blood flow by means of a number of mechanisms that may be selected from the group consisting of: via a classic piston compression mechanism; via a suction mechanism piston-type active decompression mechanism; via a pneumatically inflatable cuff or bladder; via a pneumatically inflatable cuff or bladder constrained within a non-distensible outer belt; via a series of pneumatic inflatable linear tubes constrained within a non-distensible outer belt; tourniquet of the extremities; and/or pulsation or counterpulsation of the extremities via pneumatically inflatable circumferential cuffs on the arms and legs.

Biomarker inputs that may be used by the system for control of the hemodynamic or defibrillatory subsystems may be one or more selected from the list consisting of: ET-$CO_2$; ECG; ECG derived secondary or tertiary indicators such as heart rate variability; ECG derived power spectra related indictors; ECG amplitude derived indicators; current location of hemodynamic components with respect to the patient, i.e. depth of compression; current status of pneumatic components, i.e. vest state of inflation; indicators of tissue status, i.e. near-infrared spectroscopy-like technologies; and/or indicators of ventilatory status, i.e. airway pressure.

A play-the-winner sequence in the control subsystem, such as the play-the-winner system described in FIG. 6, could be used to optimize the system and sub-system configuration, as shown and described in FIG. 7. In a particular variation, the keep-the-change/reject-the-change decision could be based on a delta AMSA/ET-$CO_2$ heuristic. Specifically, the current AMSA/ET-$CO_2$ measurements can be defined as a baseline. The next hemodynamic subsystem or subsystem performance parameter change can be added into the current system configuration. At a specified time interval (i.e. 10, 20, or 30 seconds) after the change, the AMSA/ET-$CO_2$ can again be measured, and the change (delta=current−baseline) calculated. This value can be utilized by the processor to either incorporate the most recent change into the current configuration, or reject it and move on to the next change in the precision adaptive sequence. An increase in the AMSA/ET-$CO_2$ (equal to or above a predefined threshold) can result in incorporation of the most recent change into the current configuration. A decrease (or absence of increase equal to or above the threshold), can result in rejection of the most recent configuration change and progression to the next possible hemodynamic enhancement in the precision adaptive sequence.

An automated system that combines and integrates multimodal hemodynamic and defibrillatory capabilities may further incorporate:

A. Transthoracic countershock can be applied while allowing the chest compressions of CPR to continue uninterrupted.
B. The pattern of mechanical or pneumatic hemodynamic forces can be varied so as to enhance the efficacy of countershock.
C. The gel electrodes (either adhesive or non-adhesive) can be incorporated into some or all of the patient-facing components of the automated CPR system.
D. For piston-based components, the electrodes can be incorporated into the patient-facing portion of the piston or suction cup and the patient-facing portion of the backboard.
E. For circumferential constricting components, the electrodes can be incorporated into the patient-facing surface of the band, vest, or pneumatic components.
F. The pattern of mechanical forces can be adapted to enhance the efficacy of defibrillation.
G. The control system for defibrillation can time the shock to the optimal phase of CPR just after release of compression.
H. The control system for defibrillation can time the shock to the optimal phase of assisted ventilation at or near end-expiration.
I. The patient-facing mechanical or pneumatic components can selectively push on the gel electrodes so as to lower transthoracic resistance, and the control system can time this application of force to the moment of defibrillation.
J. The patient-facing, pre-installed adhesive defibrillation electrodes can be in a configuration that allows dual, triple, or N simultaneous or sequential defibrillation optimized with respect to the CPR and ventilatory cycles.
K. The antero-posterior chest compression capability can be coordinated with the countershock subsystem such that the antero-posterior distance can be minimized at the time of defibrillation.
L. Select combinations of electrodes such that multiple paths across the chest can be utilized.
M. Select combinations of electrodes such that two counter shocks at a 90° angle to one another can be applied simultaneously.
N. Altering the selection of electrodes such that the pathway of current flow through the chest can start in one or more vectors and transitions into a different set of vectors.

In piston-type integrated CPR systems, the countershock electrodes may be on various patient-facing surfaces, including: the piston; the suction cup in active decompression systems; the backboard; and/or struts on either side of the patient's thorax intended for stabilization or additional thoracic compression.

In circumferential thoracic constriction-type integrated CPR systems, the countershock electrodes may be on various patient-facing surfaces including: one or more of the pneumatic bladders; the pneumatic vest; one or more constricting belts; struts on either side of the patient's thorax intended for stabilization or additional thoracic compression; the backboard; and/or a pneumatic bladder between the patient and the backboard.

The electrical control system for the countershock circuitry may measure one or more of: thoracic resistance, capacitance, impedance, or current flow. It might also receive status updates from one or more of the effector subsystems. Such a control system could allow: electrical countershock without interruption in mechanical chest compression or constriction; electrical countershock during the optimal portion of mechanical chest compression or constriction; electrical countershock optimized by the measurement of one or more of thoracic resistance, capacitance, impedance, or current flow; electrical countershock at the optimal portion of the ventilatory cycle; optimization of the electrical countershock by applying current through a selected subset of the patient-facing electrodes; adjustment of the force, location or timing parameters of chest compression or constriction so as to optimize one or more of thoracic resistance, capacitance, impedance, or current flow; and/or adjustment of the parameters of synchronized ventilation so as to optimize one or more of thoracic resistance, capacitance, impedance, or current flow.

The countershock electrodes can be adhesive gel electrodes that can be a disposable component that is pre-manufactured so as to be easily inserted into or removed from the patient-facing mechanical or pneumatic components.

Sensory signals that input into the electrical components and/or circuitry for the purpose of optimization and or synchronization of mechanical CPR or electrical defibrillation may originate from one or more of: the electrocardiogram, an accelerometer, a force transducer, $ET-CO_2$, $SPO_2$ (i.e. NIRS), plethysmography, an acoustical microphone, the mechanical or electrical subsystems of the device itself.

By way of non-limiting example, an embodiment can include a fully integrated mechanical CPR-defibrillation system that can include:

A. Hemodynamic subsystems capable of applying mechanical or pneumatic force to the chest, abdomen, or extremities. One or more hemodynamic subsystems can be chosen from a group including: a chest compression subsystem, a chest decompression subsystem, a chest constriction subsystem, and abdominal compression decompression subsystem, ventilatory subsystem, and extremity subsystem.
B. An electrical countershock subsystem with a countershock controller module capable of providing shocks in either a standard or sequential pattern. The countershock subsystem and its associated electronics may be physically integrated into the device, or it can be separate, with or without monitor, connected to the device by a cable. The electrical countershock electrodes can be physically integrated into the patient-facing portions of the hemodynamic components, in particular the thoracic circumferential constricting subsystem, for example, as shown in FIGS. 2A, 3, 4, and 5.
C. Biomarker subsystems capable of measuring patient or organ status. One or more biomarker or system status input subsystems chosen from a group including: ECG, ECG derived biomarkers such as AMSA, $ET-CO_2$, indicators of tissue oxygenation or energetics (i.e. NIRS).
D. Gel electrode contact pressure subsystem capable of pneumatically or mechanically applying pressure to the adhesive gel electrodes.
E. A combination countershock electrode and attached pneumatic bladder. Inflation of the bladder selectively increases electrode contact pressure.
F. A device-status capability within or in connected to the control subsystem and able to measure the location, direction, force or pressure for each of the hemodynamic subsystems. One or more measurements of subsystem status chosen from a group including: the chest compression subsystem, the chest decompression subsystem, the chest constriction subsystem, the abdominal compression-decompression subsystem, the ventilatory system, and the extremity subsystem.

G. A control subsystem capable of controlling each hemodynamic subsystem based on the biomarker feedback and system status measurements. The control subsystem can execute predefined precision adaptive sequences.

Various combinations of a control processor, measurement of subsystem status, and a play-the-winner heuristic sequence, may be combined. Further, combination of adaptive optimization sequences with a mechanical-pneumatic and countershock subsystems can allow for sequences and configurations that incorporates a substantial number of advantages described herein.

In such a configuration and sequence, the system can start with:

A. Standard sternal compressions derived from current American heart Association guidelines. In 2017, this was a depth of at least 5 cm in 70 kg adults and a rate of 100 compressions per minute. This is 600 ms for each compression-decompression cycle. At a 50% duty cycle, this is 300 ms compression phase and 300 ms decompression phase.

B. Baseline measurement of $ET-CO_2$ from an $ET-CO_2$ meter and ECG derived biomarkers from ECG. Then, based on the described play-the-winner sequence, potentially add:

C. Active decompression of the sternum to an anterior displacement of 10% greater than the starting anteroposterior diameter. In normal-sized adults, 200-400 N of force may be required to achieve this displacement. Then, based on the described play-the-winner sequence, potentially add:

D. Circumferential pneumatic thoracic constriction simultaneous with each sternal compression. Vest pneumatic pressure would be between 180 and 250 mm Hg. Then, based on the described play-the-winner sequence, potentially add:

E. Anterior abdominal pneumatic counterpulsation 106 during the 300 ms relaxation phases of the chest compression-constriction cycle. This may be achieved with a pneumatic bladder or series of bladders cyclically inflated to pressures 180- and 250-mm Hg. and constrained within a non-dispensable belt.

When ECG-AMSA indicates that the oxygen and energetic state of the myocardium had improved to a level sufficient for defibrillation with ROSC, the following events can occur in a coordinated fashion, as shown an described in FIG. 8: the ventilation subsystem can discontinue ventilation at end expiration; the contact pressure subsystem can pneumatically or mechanically apply pressure to the electrodes; and the countershock subsystem can apply standard or alternative defibrillation (i.e. simultaneous or sequential) during the 200 ms just after release of chest compression and constriction.

In various embodiments, the specific subsystems utilized (i.e. chest compression, chest decompression, chest constriction, abdominal counterpulsation), and performance parameters of the hemodynamic subsystems (i.e. force, distance, pressure, intervals) may be optimized by way of one or more play-the-winner heuristic sequences.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. By way of non-limiting examples, the ARS may incorporate any type of defibrillation or countershock waveform, including biphasic and monophasic. The ARS may incorporate any type of mechanical or pneumatic technology as a source of force or pressure within the CPR system. The ARS may incorporate any type of countershock electrode upon or within the patient. The ARS may incorporate any pattern of electrodes upon or within the patient. The ARS may incorporate any type of control system for the subsystems, including but not limited to: electronic circuits, electronic controllers, or computers. The ARS may incorporate any one of a multiplicity of sensors for adaptive modification of the subsystems. By way of illustration but not limitation, these sensor measurements may include: the electrocardiogram, VF median frequency, VF power spectra, thoracic impedance, thoracic resistance, current flow, ET-CO2, measurements of perfusion, measurements of organ or patient status. Accordingly, this description is meant to be taken only by way of example, and not to otherwise limit the scope of this invention. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Accordingly, this description is meant to be taken only by way of example, and not to otherwise limit the scope of this invention.

What is claimed is:

1. An automated resuscitation system (ARS) comprising:
   at least one means for compression of the chest that produces forward blood flow;
   a countershock defibrillation subsystem;
   a plurality of countershock electrodes on patient facing portions of the ARS;
   electrode contact pressure enhancers; and
   a control system adapted to synchronize chest compressions and countershocks, wherein the control system alters the patterns of ventilation and electrical countershock such that electrical countershock is within one second of end-expiration.

2. The ARS of claim 1, wherein the electrode contact pressure enhancers are at least a portion of the at least one the means for compression of the chest that produces forward blood flow.

3. The ARS of claim 1, wherein the at least one means for compression of the chest comprises bladders adapted to encircle all or a portion of a patient's chest.

4. The ARS of claim 1, further comprising a ventilation subsystem, wherein the control system synchronizes the ventilation subsystem and the countershock defibrillation subsystem.

5. The ARS of claim 1, further comprising at least one biomarker sensor providing biomarker information, and wherein the controller uses the biomarker information in determining a pattern of synchronization of the chest compressions and countershocks.

6. The ARS of claim 1, wherein the plurality of countershock electrodes further comprises at least two pairs of countershock electrodes, and wherein defibrillation is achieved by multiple current paths across the chest.

7. The ARS of claim 1, wherein the countershock electrodes are incorporated into patient facing surfaces of one or more of components selected from the list consisting of pistons, circumferential constricting bladders, constricting series of bladders, constricting bands, a suction cup, a backboard, or struts on either side of the patient's thorax.

8. The ARS of claim 1, wherein the control system is adapted to increase a contact pressure of the countershock electrodes at a time of countershock.

9. The ARS of claim 1 wherein the at least one means for compression inflates a circumferential series of bladders, wherein portions of the circumferential series of bladders over the countershock electrodes may be individually inflated.

10. The ARS of claim 1, wherein the control system is adapted to increase a force or alter a pattern of compression of the chest based on one or more biomarker measurements selected from a group consisting of thoracic electrical resistance, ECG, EN-tidal $CO_2$, and ventricular fibrillatory frequency distribution.

11. The ARS of claim 1, wherein the control system is adapted to apply countershock current along a first vector, and then transition to apply countershock current along a second vector.

12. The ARS of claim 1, wherein the means adapted for applying pressure to the chest is adapted to deliver a first compression-decompression pattern optimized for producing forward blood flow, and a second compression-decompression pattern optimized for increasing the efficacy of electrical countershock.

13. The automated resuscitation system ARS of claim 1, wherein an overall pattern of the compression may be released by a first portion of the at least one means for compression so as to allow onset of the chest decompression, and wherein compression is maintained in a second portion of the at least one means for compression, the second portion located over the countershock defibrillation electrodes, so as to enhance electrode contact pressure.

14. The ARS of claim 11, wherein the countershock electrodes are incorporated into the electrode contact pressure enhancers.

15. The ARS of claim 1 further comprising an esophageal subsystem comprising one or more of balloons, countershock electrodes, and sensors.

16. The ARS of claim 1, wherein the first portion of the plurality of means adapted for applying pressure to the chest are configured for insertion of electrodes that are removable and disposable.

17. An automated resuscitation system (ARS) comprising:
at least one means adapted for applying pressure to a chest to produce blood flow;
a countershock defibrillator subsystem;
a plurality of countershock electrodes on patient facing portions of the ARS;
a ventilation subsystem; and
a control system adapted to synchronize chest compressions, countershocks, and ventilation, wherein that electrical countershock occurs at end-expiration lung volume.

18. An automated resuscitation system (ARS) comprising:
at least one means for compression of the chest that produces forward blood flow;
a countershock defibrillation subsystem;
a plurality of countershock electrodes on patient facing portions of the ARS;
electrode contact pressure enhancers; and
a control system adapted to synchronize chest compressions and countershocks, wherein the at least one means for compression inflates a circumferential series of bladders, wherein portions of the circumferential series of bladders over the countershock electrodes may be individually inflated.

19. An automated resuscitation system (ARS) comprising:
at least one means for compression of the chest that produces forward blood flow;
a countershock defibrillation subsystem;
a plurality of countershock electrodes on patient facing portions of the ARS;
electrode contact pressure enhancers; and
a control system adapted to synchronize chest compressions and countershocks, wherein the means adapted for applying pressure to the chest is adapted to deliver a first compression-decompression pattern optimized for producing forward blood flow, and a second compression-decompression pattern optimized for increasing the efficacy of electrical countershock.

20. An automated resuscitation system (ARS) comprising:
at least one means for compression of the chest that produces forward blood flow;
a countershock defibrillation subsystem;
a plurality of countershock electrodes on patient facing portions of the ARS;
electrode contact pressure enhancers; and
a control system adapted to synchronize chest compressions and countershocks, wherein an overall pattern of the compression may be released by a first portion of the at least one means for compression so as to allow onset of the chest decompression, and wherein compression is maintained in a second portion of the at least one means for compression, the second portion located over the countershock defibrillation electrodes, so as to enhance electrode contact pressure.

\* \* \* \* \*